United States Patent
Aoyama

(10) Patent No.: US 11,979,543 B2
(45) Date of Patent: May 7, 2024

(54) MEDICAL IMAGE PROCESSING APPARATUS

(71) Applicant: FUJIFILM Corporation, Tokyo (JP)

(72) Inventor: Tatsuya Aoyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 519 days.

(21) Appl. No.: 17/013,992

(22) Filed: Sep. 8, 2020

(65) Prior Publication Data

US 2020/0402238 A1    Dec. 24, 2020

Related U.S. Application Data

(63) Continuation of application No. PCT/JP2019/014717, filed on Apr. 3, 2019.

(30) Foreign Application Priority Data

Apr. 11, 2018 (JP) ................. 2018-076060

(51) Int. Cl.
G06K 9/00 (2022.01)
A61B 1/00 (2006.01)
G06F 18/22 (2023.01)
G06T 5/92 (2024.01)
G06T 7/00 (2017.01)
(Continued)

(52) U.S. Cl.
CPC ..... *H04N 1/6027* (2013.01); *A61B 1/000094* (2022.02); *G06F 18/22* (2023.01); *G06T 5/92* (2024.01); *G06T 7/0012* (2013.01); *G06T 7/90* (2017.01); *G06V 10/141* (2022.01); *G06V 10/145* (2022.01); *G06V 10/60* (2022.01);
(Continued)

(58) Field of Classification Search
None
See application file for complete search history.

(56) References Cited

U.S. PATENT DOCUMENTS

2002/0131634 A1    9/2002    Weibrecht et al.
2010/0007724 A1    1/2010    Takayama
(Continued)

FOREIGN PATENT DOCUMENTS

| CN | 103501681 A | 1/2014 |
| CN | 103717118 A | 4/2014 |

(Continued)

OTHER PUBLICATIONS

Gu et al., "Image enhancement based on in vivo hyperspectral gastroscopic images: a case study" (Year: 2016).*

(Continued)

*Primary Examiner* — Soo Jin Park
(74) *Attorney, Agent, or Firm* — Studebaker & Brackett PC

(57) ABSTRACT

Provided is a medical image processing apparatus that generates a color image by using one type of specific color image obtained by imaging a subject with specific monochromatic light. The medical image processing apparatus (10) includes an image acquisition unit (medical image acquisition unit (11)) that acquires a specific color image (56) obtained by imaging a subject with specific monochromatic light, and a color image generation unit (12) that generates a color image from the specific color image by assigning the specific color image (56) to a plurality of color channels and adjusting a balance of each of the color channels.

15 Claims, 17 Drawing Sheets

(51) Int. Cl.
  *G06T 7/90* (2017.01)
  *G06V 10/141* (2022.01)
  *G06V 10/145* (2022.01)
  *G06V 10/60* (2022.01)
  *G16H 30/20* (2018.01)
  *H04N 1/60* (2006.01)

(52) U.S. Cl.
  CPC ... *G16H 30/20* (2018.01); *G06T 2207/10024* (2013.01); *G06T 2207/30024* (2013.01)

(56) References Cited

U.S. PATENT DOCUMENTS

| | | |
|---|---|---|
| 2012/0328175 A1 | 12/2012 | Watanabe |
| 2013/0176411 A1 | 7/2013 | Igarashi et al. |
| 2013/0324797 A1 | 12/2013 | Igarashi et al. |
| 2018/0289246 A1* | 10/2018 | Tabata .................. A61B 1/044 |
| 2020/0260940 A1* | 8/2020 | Kutsuma .............. A61B 1/0655 |

FOREIGN PATENT DOCUMENTS

| | | |
|---|---|---|
| EP | 2687145 A1 | 1/2014 |
| EP | 2719317 A1 | 4/2014 |
| JP | S60-202318 A | 10/1985 |
| JP | H4-357929 A | 12/1992 |
| JP | H06-269409 A | 9/1994 |
| JP | 2002-199241 A | 7/2002 |
| JP | 2003-093338 A | 4/2003 |
| JP | 2003-093342 A | 4/2003 |
| JP | 3586157 B2 | 11/2004 |
| JP | 2008-042273 A | 2/2008 |
| JP | 2008-058461 A | 3/2008 |
| JP | 2010-36017 A | 2/2010 |
| JP | 2013-218136 A | 10/2013 |
| JP | 2016-039485 A | 3/2016 |
| JP | 2017-104609 A | 6/2017 |
| JP | 6269409 B2 | 1/2018 |
| WO | 2011/118288 A1 | 9/2011 |
| WO | 2013/042395 A1 | 3/2013 |
| WO | 2013/145407 A1 | 10/2013 |
| WO | 2017/203996 A1 | 11/2017 |

OTHER PUBLICATIONS

An Office Action; "Notice of Reasons for Refusal," mailed by the Japanese Patent Office dated Oct. 26, 2021, which corresponds to Japanese Patent Application No. 2020-513213 and is related to U.S. Appl. No. 17/013,992 with English translation.

An Office Action; "Decision of Refusal," mailed by the Japanese Patent Office on Nov. 22, 2022, which corresponds to Japanese Patent Application No. 2020-513213 and is related to U.S. Appl. No. 17/013,992; with English language translation.

International Search Report issued in PCT/JP2019/014717 dated Jul. 2, 2019.

Written Opinion issued in PCT/JP2019/014717; dated Jul. 2, 2019.

An Office Action; "Notice of Reasons for Refusal," mailed by the Japanese Patent Office dated Jun. 14, 2022, which corresponds to Japanese Patent Application No. 2020-513213 and is related to U.S. Appl. No. 17/013,992 with English translation.

An Office Action mailed by China National Intellectual Property Administration dated Feb. 15, 2023, which corresponds to Chinese Patent Application No. 201980023192.9 and is related to U.S. Appl. No. 17/013,992; with English language translation.

An Office Action mailed by China National Intellectual Property Administration dated Jun. 13, 2023, which corresponds to Chinese Patent Application No. 201980023192.9 and is related to U.S. Appl. No. 17/013,992; with English language translation.

* cited by examiner

MEDICAL IMAGE PROCESSING APPARATUS

CROSS-REFERENCE TO RELATED APPLICATIONS

This application is a Continuation of PCT International Application No. PCT/JP2019/014717 filed on Apr. 3, 2019, which claims priority under 35 U.S.C § 119(a) to Japanese Patent Application No. 2018-076060 filed on Apr. 11, 2018. Each of the above application(s) is hereby expressly incorporated by reference, in its entirety, into the present application.

BACKGROUND OF THE INVENTION

1. Field of the Invention

The present invention relates to a medical image processing apparatus that performs processing using medical images.

2. Description of the Related Art

In the related art, an apparatus that acquires an image including a subject image (hereinafter, referred to as a medical image) among apparatuses relevant to medical care (hereinafter, referred to as a medical apparatus) presents the acquired medical image to a doctor. In addition, the medical apparatus that presents a color image may support a diagnosis by not only presenting the acquired medical image but also presenting the medical image whose tone and the like have been adjusted.

For example, in an endoscope apparatus that is a medical apparatus, in a case where a subject is imaged using two types of so-called narrow-band light (light having an extremely narrow limited wavelength band), an image is displayed in which the surface layer of the mucous membrane is adjusted to a reddish color and the blood vessel at a deep position under the mucous membrane is adjusted to a bluish color (JP3586157B). In this image, blood vessels in the surface layer of the mucous membrane are more easily observed than in an image in which a subject is naturally imaged using white light (so-called white light image).

It is known that another endoscope apparatus presents an image in which a lesion or the like is highlighted by properly selecting an image to be assigned to each of RGB channels of an image to be displayed (JP1992-357929A (JP-H4-357929A)). In recent years, there is also known an endoscope apparatus that generates an image in which a lesion or the like is easily observed by highlighting a difference in a specific hue with respect to a color image having each RGB channel components (JP2017-104609A).

SUMMARY OF THE INVENTION

In the endoscope apparatus, a color image is generated by assigning a plurality of types of images having different wavelength bands of illumination light to each RGB channels, as in the endoscope apparatuses of JP3586157B, JP1992-357929A (JP-H4-357929A), JP2017-104609A, and the like.

However, in displaying a color image and the like, in a case where the color image is generated using a plurality of types of images with different imaging conditions, the visibility of the tissue, lesion, or the like, which is an observation target, may be reduced as compared with the original images used to generate the color image. This is because the tissue or lesion is drawn differently depending on the imaging conditions, and the tissue or lesion that is drawn with high visibility under a specific imaging condition is buried in the drawing of the image captured under another imaging condition in the color image generated using a plurality of types of images.

An object of the present invention is to provide a medical image processing apparatus that generates a color image in which ease of observation of a subject image is maintained or ease of observation of the subject image is improved by using one type of specific color image obtained by imaging a subject with specific monochromatic light.

A medical image processing apparatus comprises an image acquisition unit that acquires a specific color image obtained by imaging a subject with specific monochromatic light, and a color image generation unit that generates a color image from the specific color image by assigning the specific color image to a plurality of color channels and adjusting a balance of each of the color channels.

It is preferable that the color image generation unit adjusts gradation of each of the color channels.

It is preferable that the color image generation unit adjusts a gain applied to the specific color image in a case where the specific color image is assigned to the color channels.

It is preferable that the color image generation unit changes the balance of the color channels for each pixel or for each region including a plurality of pixels.

It is preferable that the color image generation unit adjusts the balance of the color channels depending on a density of a subject image.

It is preferable that the color image generation unit increases a distance between a color of a relatively low density portion of the subject image and a color of a relatively high density portion of the subject image, in an $L^*a^*b^*$ color space.

It is preferable that the color image generation unit adjusts the balance of the color channels depending on a frequency of a subject image.

It is preferable that the color image generation unit increases a distance between a color of a relatively low frequency component of the subject image and a color of a relatively high frequency component of the subject image, in an $L^*a^*b^*$ color space.

It is preferable that in a case where a subject image includes a blood vessel and a mucous membrane, the color image generation unit increases a color difference between the blood vessel and the mucous membrane with respect to the subject image in the specific color image.

It is preferable that in a case where a subject image includes a blood vessel and a mucous membrane, the color image generation unit increases a difference in brightness between the blood vessel and the mucous membrane with respect to the subject image in the specific color image.

It is preferable that in a case where a subject image includes a mucous membrane, the mucous membrane is green.

It is preferable that the color image generation unit increases a distance between a color of a relatively high density and high frequency portion of a subject image and a color of a relatively low density and low frequency portion of the subject image, in an $L^*a^*b^*$ color space.

It is preferable that the monochromatic light is violet light, blue light, or green light.

It is preferable that the medical image processing apparatus further comprises a storage unit that stores a plurality of adjustment patterns related to the balance of the color channels, and a selection unit that selects the adjustment pattern, the color image generation unit generates the color image according to the adjustment pattern selected by the selection unit, and in a case where the selection unit newly selects the adjustment pattern, the color image generation unit switches an adjustment method of the color channels to an adjustment method according to the adjustment pattern newly selected by the selection unit.

The medical image processing apparatus according to the aspect of the present invention can generate a color image in which ease of observation of a subject image is maintained or ease of observation of the subject image is improved by using one type of specific color image obtained by imaging a subject with specific monochromatic light.

DESCRIPTION OF THE PREFERRED EMBODIMENTS

First Embodiment

Figure 1:
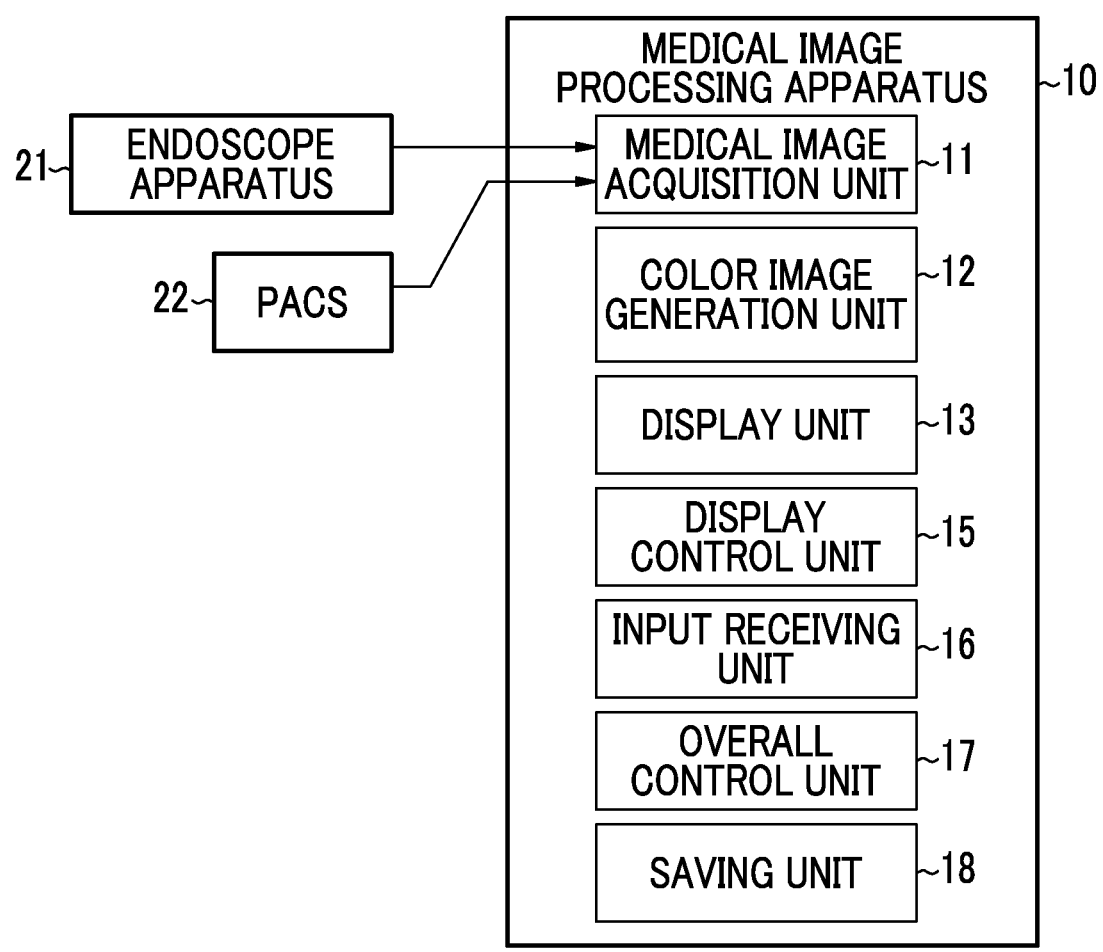
FIG. 1 is a block diagram of a medical image processing apparatus.

As shown in FIG. 1, a medical image processing apparatus 10 comprises a medical image acquisition unit 11, a color image generation unit 12, a display unit 13, a display control unit 15, an input receiving unit 16, an overall control unit 17, and a saving unit 18.

The medical image acquisition unit 11 acquires a medical image including a subject image, directly from an endoscope apparatus 21 or the like that is a medical apparatus, or through a management system such as a picture archiving and communication system (PACS) 22, or other information systems. The medical image is a still image or a motion picture (a so-called examination motion picture). In a case where the medical image is a motion picture, the medical image acquisition unit 11 can acquire a frame image forming a motion picture as a still image after examination. In addition, in a case where the medical image is a motion picture, display of the medical image includes not only displaying a still image of one representative frame forming the motion picture but also reproducing the motion picture once or multiple times. In addition, the medical image acquired by the medical image acquisition unit 11 includes an image automatically captured by a medical apparatus such as the endoscope apparatus 21 regardless of a capturing instruction of a doctor, in addition to an image captured by the doctor using a medical apparatus such as the endoscope apparatus 21.

In the case of being capable of acquiring a plurality of medical images, the medical image acquisition unit 11 can selectively acquire one or a plurality of medical images among these medical images. In addition, the medical image acquisition unit 11 can acquire a plurality of medical images acquired in a plurality of different examinations. For example, it is possible to acquire one or both of a medical image acquired in an examination performed in the past and a medical image acquired in the latest examination. That is, the medical image acquisition unit 11 can acquire a medical image optionally.

In the present embodiment, the medical image processing apparatus 10 is connected to the endoscope apparatus 21 to acquire a medical image from the endoscope apparatus 21. That is, in the present embodiment, the medical image is an endoscopic image. Then, the medical image acquisition unit 11 functions as at least an image acquisition unit that acquires a specific color image obtained by imaging a subject with specific monochromatic light. The "specific monochromatic light" refers to light having a part of a wavelength band in which an imaging device (image sensor or the like) used for imaging a subject has sensitivity as a whole. Therefore, in a case where the imaging device has sensitivity to visible light, light having a narrower wavelength band than the entire visible light, such as red light, green light, or blue light, is "specific monochromatic light". In a case where the imaging device has sensitivity to ultraviolet light, infrared light, X-rays, or the like, the ultraviolet light, infrared light, X-rays, or the like can also be "specific monochromatic light".

More specifically, in the present embodiment, the medical image acquisition unit 11 acquires, as a specific color image, an image obtained by imaging a subject with monochromatic narrow-band light from the endoscope apparatus 21 in order to generate a color image. The "monochromatic" means having a wavelength band that can be regarded as having substantially one wavelength in relation to an imaging device (wavelength band of a color filter or the like) or image process to be performed. For example, red light, green light, blue light, violet light, and the like are each monochromatic light. In a case where one pixel receives first monochromatic light and second monochromatic light having a wavelength band different from that of the first monochromatic light, mixed light of the first monochromatic light and the second monochromatic light is "monochromatic". The same applies to mixed light in which three or more monochromatic lights are combined. The "narrow-band light" is, for example, monochromatic light having an extremely narrow wavelength band of, for example, about ±20 nm, preferably about ±10 nm with respect to a center wavelength. In a case where mixed light is used, for example, in a case where each monochromatic light to be mixed is narrow-band light, at least the mixed light is monochromatic narrow-band light as a whole.

Figure 2:
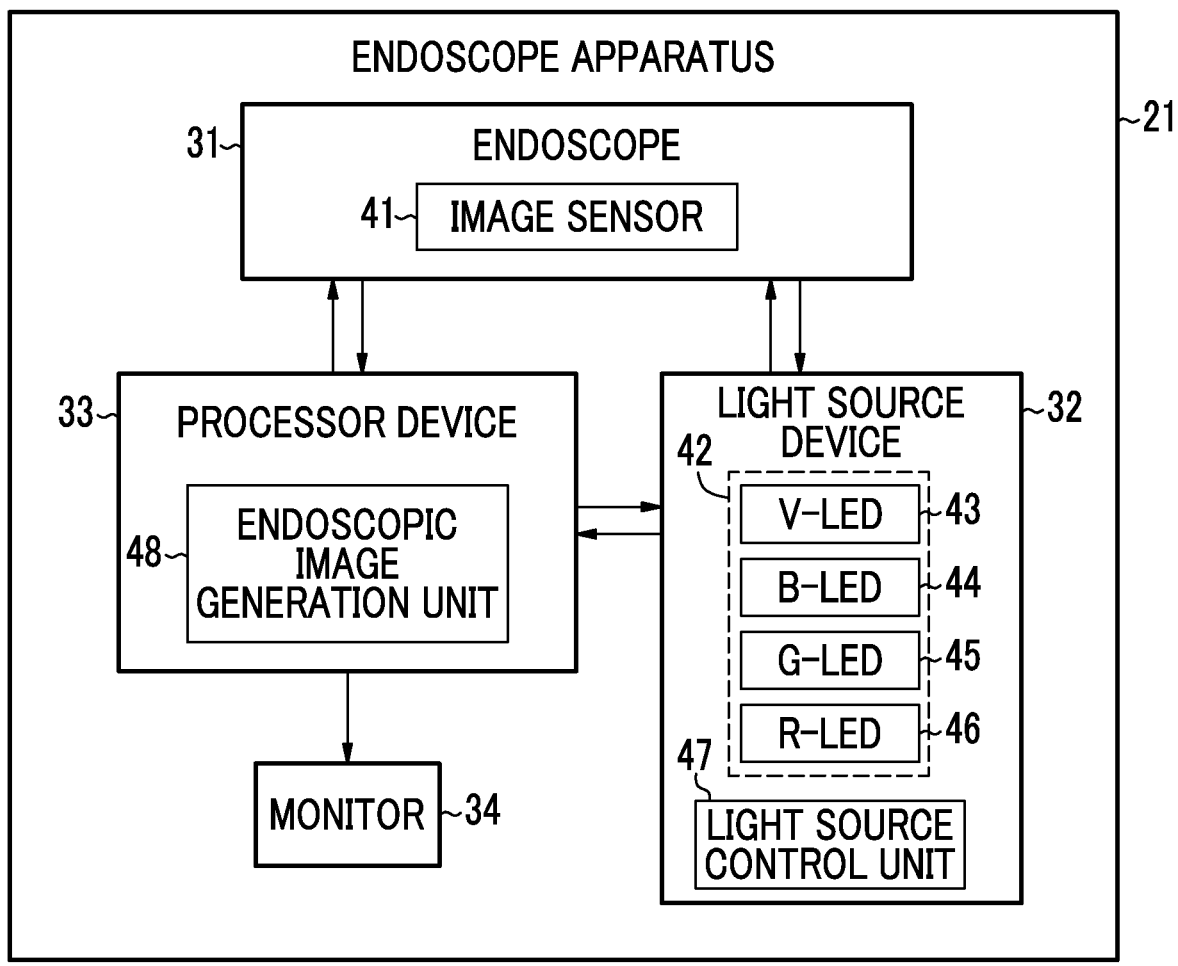
FIG. 2 is a block diagram of an endoscope apparatus.

As shown in FIG. 2, in the present embodiment, the endoscope apparatus 21 to which the medical image processing apparatus 10 is connected has an endoscope 31 that emits at least one of light in a white wavelength band or light in a specific wavelength band to image a subject, a light source device 32 that emits illumination light to the inside of the subject through the endoscope 31, a processor device 33, and a monitor 34 for displaying an endoscopic image or the like captured using the endoscope 31.

The endoscope 31 comprises an image sensor 41 that images the subject using illumination light reflected or scattered by the subject, or fluorescence emitted by the subject or a medicine or the like administered to the subject. The image sensor 41 is, for example, a complementary metal oxide semiconductor (CMOS) color sensor (a sensor having a color filter). In the present embodiment, the image sensor 41 is a primary color system color sensor having any of an R color filter (red color filter), a G color filter (green color filter), or a B color filter (blue color filter) for each pixel. Hereinafter, a pixel having an R color filter is referred to as an R pixel, a pixel having a G color filter is referred to as a G pixel, and a pixel having a B color filter is referred to as a B pixel.

A charge coupled device (CCD) image sensor can be used as the image sensor 41. The image sensor 41 may be provided with a complementary color filter, or may be provided with a pixel having no color filter. In addition, a monochrome sensor having no color filter can be used as the image sensor 41. In a case where a monochrome sensor is used as the image sensor 41, a color filter separate from the image sensor 41 can be used in combination, as necessary.

The light source device 32 includes a light source unit 42 and a light source control unit 47. The light source unit 42 emits a plurality of types of illumination light having different spectra. The light source unit 42 comprises, for example, a light emitting device such as a light emitting diode (LED), a laser diode (LD), or a xenon lamp. In addition, the light source unit 42 comprises a prism, a mirror, an optical fiber, an optical filter for adjusting a wavelength band or a light amount, and the like, as necessary. In the present embodiment, the light source unit 42 comprises a V-LED 43, a B-LED 44, a G-LED 45, and an R-LED 46. The V-LED 43 emits violet light having a center wavelength of 405 nm and a wavelength band of 380 nm to 420 nm. The B-LED 44 emits blue light having a center wavelength of 460 nm and a wavelength band of 420 nm to 500 nm. The G-LED 45 emits green light having a wavelength band of 480 nm to 600 nm. The R-LED 46 emits red light having a center wavelength of 620 nm to 630 nm and a wavelength band of 600 nm to 650 nm.

The light source control unit 47 controls a light emitting source included in the light source unit 42, and generates illumination light to be used by the endoscope 31 to image a subject. In a case where the light source unit 42 includes a plurality of light emitting devices, the light source control unit 47 can individually control the light emission timing and the light emission amount of each light emitting device. Therefore, the light source device 32 can supply the plurality of types of illumination light having different spectra to the endoscope 31 at any timing and any intensity. For example, in the present embodiment, the light source device 32 can emit violet light, blue light, green light, red light, or light obtained by mixing two or more of these colors at any intensity ratio in addition to white light under the control performed by the light source control unit 47, as illumination light at any timing and any intensity. In addition, the light source device 32 can emit light having a specific narrow wavelength band (a so-called narrow-band light) as illumination light due to characteristics of a light emitting device or use of an optical filter. For example, light in a shorter wavelength band than the green wavelength band, in particular, light in a blue band or a violet band of the visible range can be emitted. In the present embodiment, the violet light emitted by the V-LED 43 is narrow-band light. Therefore, by turning on only the V-LED 43, the light source unit 42 can emit violet light in a narrow band. On the other hand, the blue light emitted by the B-LED 44, the green light emitted by the G-LED 45, and the red light emitted by the R-LED 46 are broadband light. Therefore, the light source unit 42 emits blue narrow-band light, green narrow-band light, or red narrow-band light by using an optical filter (not shown) in combination. The "broadband light" is light having a wavelength band larger than about ±20 nm with respect to a center wavelength. Since each of the violet light (violet narrow-band light) emitted by the V-LED 43, the blue light emitted by the B-LED 44, the blue narrow-band light generated from the blue light emitted by the B-LED 44, and mixed light thereof are received by the B pixel, they are "monochromatic" light (monochromatic light) in the present embodiment, and can be used to capture a specific color image.

The processor device 33 comprises an endoscopic image generation unit 48. The endoscopic image generation unit 48 acquires an endoscopic image from the image sensor 41 and generates an endoscopic image obtained by performing image processing on the endoscopic image acquired from the image sensor 41. The image sensor 41 and the endoscopic image generation unit 48 form an "endoscopic image acquisition unit" in the endoscope apparatus 21. The endoscopic image acquisition unit acquires an endoscopic image including a subject image obtained by imaging the subject using illumination light. The medical image processing apparatus 10 is connected to the processor device 33. The medical image acquisition unit 11 acquires the endoscopic image directly from the endoscopic image generation unit 48 of the endoscope apparatus 21. Here, even in a case where the medical image acquisition unit 11 acquires the endoscopic image generated by the endoscopic image generation unit 48, the medical image acquisition unit 11 acquires at least the endoscopic image output from the image sensor 41 (the original endoscopic image used by the endoscopic image generation unit 48 to generate the endoscopic image). In this manner, the medical image acquisition unit 11 acquires a specific color image obtained by imaging the subject with specific monochromatic light. In the present embodiment, in a case where a subject is imaged using illumination light including violet light emitted by the V-LED 43, the medical image acquisition unit 11 acquires a monochrome endoscopic image including data of blue pixels (pixels having a blue color filter) of the image sensor 41. Hereinafter, the monochrome endoscopic image is simply referred to as a specific color image 56 (see FIG. 4).

Figure 3:
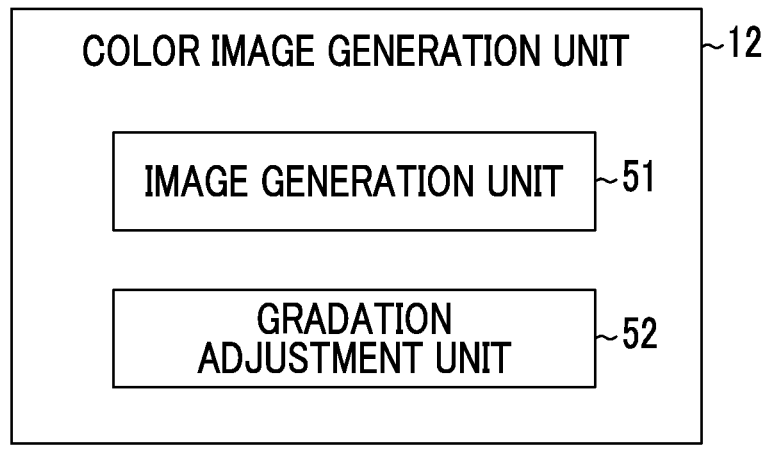
FIG. 3 is a block diagram of a medical image analysis processing unit.

The color image generation unit 12 generates a color image 57 (see FIG. 4) from the specific color image 56 by assigning the specific color image 56 acquired by the medical image acquisition unit 11 to a plurality of color channels and adjusting a balance of each of the color channels. To this end, as shown in FIG. 3, the color image generation unit 12 includes an image generation unit 51 and a gradation adjustment unit 52.

The "generating a color image from the specific color image 56" means generating a color image by using substantially one type of monochrome image in a case where the color image is generated. Therefore, in a case where a color image is generated using only the specific color image 56 without using another image whose imaging condition is different from that of the specific color image 56, it means that the color image is generated from the specific color image 56. Further, even though addition, subtraction, multiplication, division, or other calculations of another image whose imaging condition is different from that of the specific color image 56 are performed on the specific color image 56, in a case where a color image is generated using only the specific color image 56 after these calculations, the color image is generated using substantially one type of monochrome image. Accordingly, this case is also included in the "generating a color image from the specific color image 56".

Figure 4:
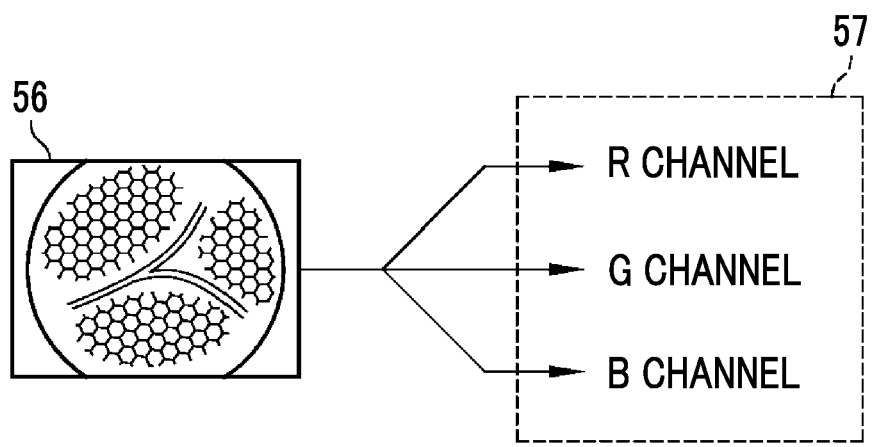
FIG. 4 is an explanatory diagram showing an operation of an image generation unit.

The color channel is a color channel forming the color image 57, and includes, for example, a red channel (hereinafter, referred to as an R channel), a green channel (hereinafter, referred to as a G channel), and a blue channel (hereinafter, referred to as a B channel). The same applies to a case where a color image is formed using other color channels in addition to or instead of these color channels. In the present embodiment, it is assumed that the color image 57 has an R channel, a G channel, and a B channel. The image generation unit 51 assigns the specific color image 56 to the plurality of color channels forming the color image. That is, as shown in FIG. 4, the image generation unit 51 assigns the specific color image 56 to the R channel, the G channel, and the B channel of the color image 57.

Figure 5:
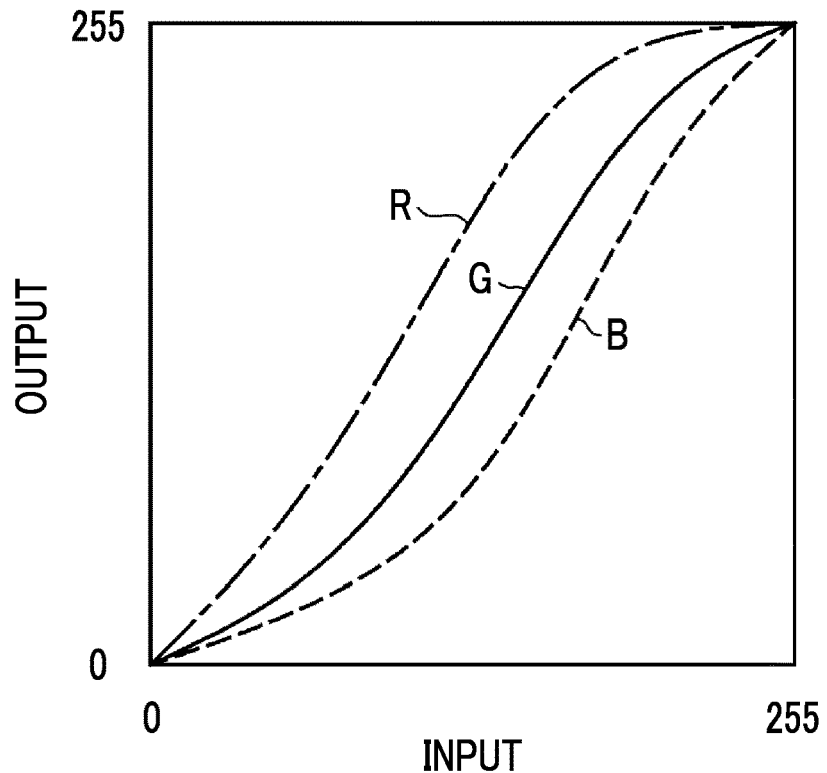
FIG. 5 is a tone curve used for gradation adjustment.

Adjustment performed by the color image generation unit 12 is adjustment of gradation of each of the color channels, and the gradation adjustment unit 52 performs the adjustment. As shown in FIG. 5, the gradation adjustment unit 52 adjusts the gradation of the color image 57 by changing the balance of each color channel of the color image 57 using a so-called tone curve. "Input" is the original specific color image 56, and "output" is the color image 57 after gradation adjustment. In the present embodiment, the output of the G channel (sign "G") is made larger than that of the B channel (sign "B"), and the output of the R channel (sign "R") is made larger than that of the G channel. That is, the tone curve is set to a balance of substantially B<G<R. In this manner, the color image 57 becomes an image having a tone close to that of the white light image.

In the present embodiment, the gradation adjustment unit 52 adjusts the balance of each color channel of the color image 57 after the image generation unit 51 assigns the specific color image 56 to each color channel. Here, the gradation adjustment unit 52 can execute balance adjustment for each specific color image 56 (a copy of the specific color image 56) assigned to each color channel before the image generation unit 51 assigns the specific color image 56 to each color channel. Further, the gradation adjustment unit 52 can execute balance adjustment by interrupting when the image generation unit 51 assigns the specific color image 56 to each color channel, that is, during the assignment processing of the specific color image 56 to each color channel.

The display unit 13 is a display for displaying the medical image acquired by the medical image acquisition unit 11 and/or the color image 57 or the like generated by the color image generation unit 12. A monitor or a display included in a device or the like to which the medical image processing apparatus 10 is connected can be shared and used as the display unit 13 of the medical image processing apparatus 10.

The display control unit 15 controls a display form of the medical image and/or the color image 57 or the like on the display unit 13. The display form is, for example, a form such as a display size, a display position, the number of displays of the color image 57 or the like, a side by side display with another image or the like, or a display or non-display of information about the subject.

The input receiving unit 16 receives inputs from a mouse, a keyboard, and other operation devices connected to the medical image processing apparatus 10. An operation of each unit of the medical image processing apparatus 10 can be controlled using the operation devices.

The overall control unit 17 controls the overall operation of each unit of the medical image processing apparatus 10. In a case where the input receiving unit 16 receives an operation input using an operation device, the overall control unit 17 controls each unit of the medical image processing apparatus 10 according to the operation input.

The saving unit 18 saves the color image 57 and/or other detection results or discrimination results, as necessary in a storage device (not shown) such as a memory included in the medical image processing apparatus 10 or a storage device (not shown) included in a medical apparatus such as the endoscope apparatus 21 or the PACS 22.

Figure 6:
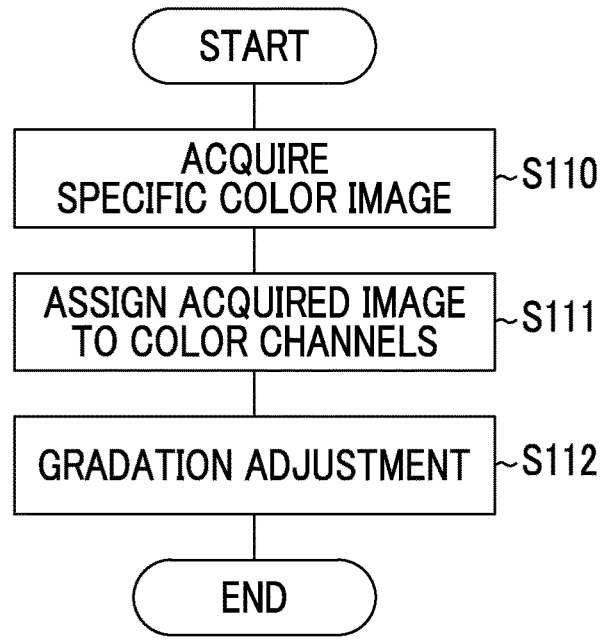
FIG. 6 is a flowchart showing a flow of generating a color image.

Hereinafter, the flow of the medical image processing apparatus 10 that generates the color image 57 and its operation will be described. As shown in FIG. 6, the medical image processing apparatus 10 uses the medical image acquisition unit 11 to acquire the specific color image 56 from the endoscope apparatus 21 (step S110). Subsequently, the color image generation unit 12 uses the image generation unit 51 to assign the acquired specific color image 56 to the R channel, the G channel, and the B channel, thereby generating the color image 57 (step S111). Even though it is called a color image 57, the color image 57 generated by the image generation unit 51 is a monochrome image having no tint because the specific color image 56 is simply assigned to each color channel. Therefore, the color image generation unit 12 uses the gradation adjustment unit 52 to adjust the gradation of the color image 57 (step S112). As a result, the color image 57 is colorized.

Figure 7:
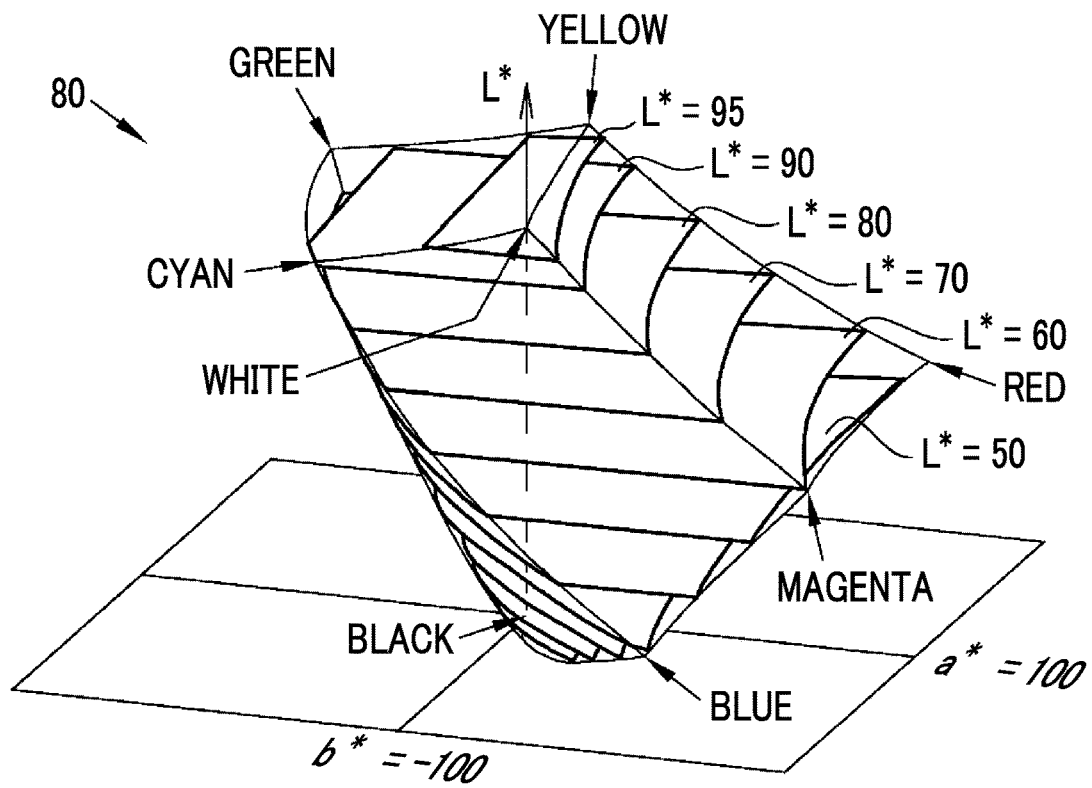
FIG. 7 is a color gamut of sRGB in an L*a*b* color space.

The international standard relating to the color space in electronic devices such as the display unit 13 is standard RGB (sRGB) defined by International Electrotechnical Commission (IEC). On the other hand, there is an L*a*b* color space as a color space considering human vision. As shown in FIG. 7, the range of colors that can be displayed on the display unit 13 or the like and that can be visually recognized by the human eye is a color gamut 80 of sRGB in the L*a*b* color space. L* represents lightness and takes a value of 0 to 100. The color on the L* axis is so-called gray scale. On the L* axis, L*=0 is "black" and L*=100 is "white". In the L*a*b* color space, both a* and b* can take a positive value, a negative value, or 0.

Figure 8:
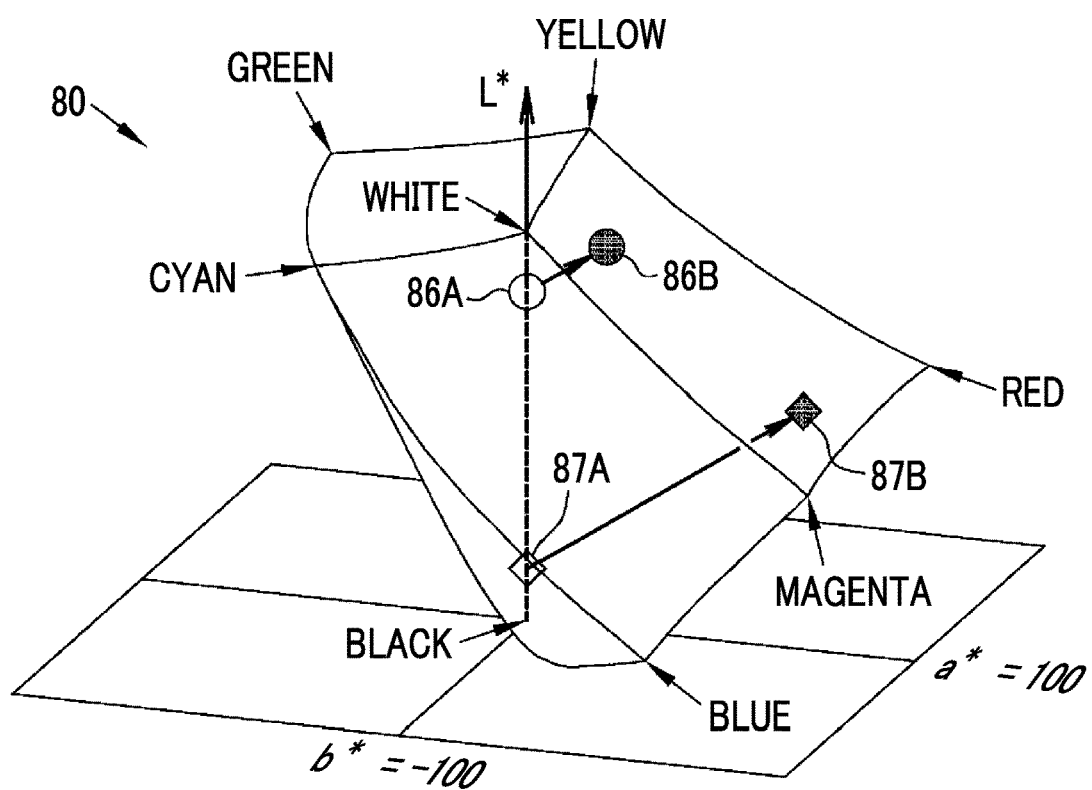
FIG. 8 is an explanatory diagram showing a relationship between gradation adjustment and color change.
Figure 9:
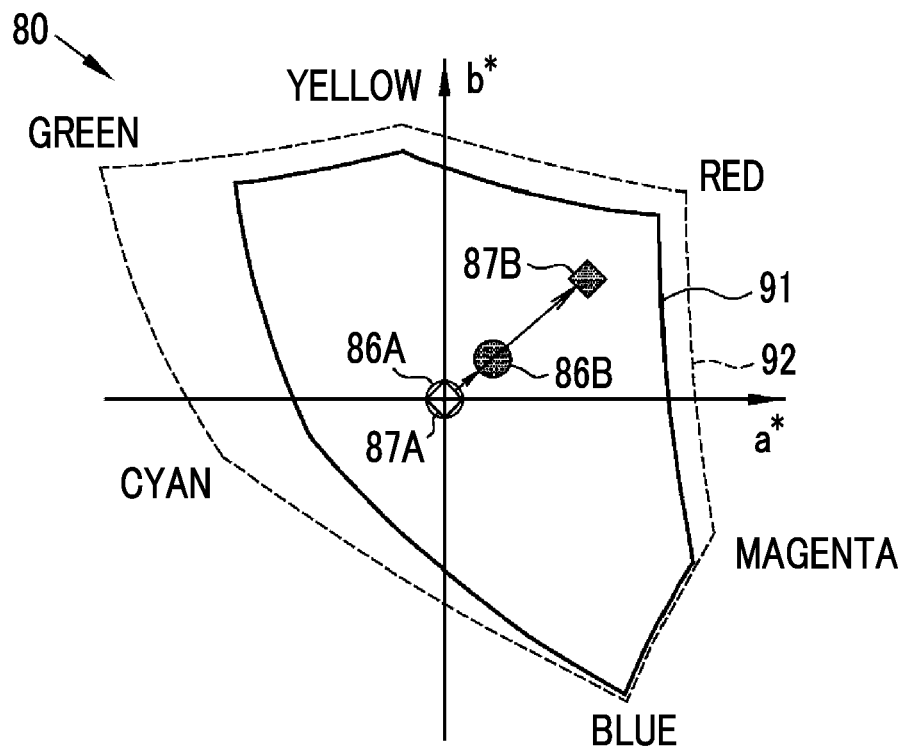
FIG. 9 is an explanatory diagram showing a relationship between gradation adjustment and color change.

In a case where it is assumed that the subject image shown in the specific color image 56 used to generate the color image 57 includes a mucous membrane and a blood vessel, the blood vessel is likely to absorb the narrow-band violet light due to hemoglobin. Therefore, in the specific color image 56, the mucous membrane is relatively white (light gray that is relatively close to white) and the blood vessel is black (dark gray that is relatively close to black). As shown in FIG. 8, in the color gamut 80, it is assumed that the color of the mucous membrane in the specific color image 56 is light gray 86A (marked by ○), and the color of the blood vessel in the specific color image 56 is dark gray 87A (marked by ◇). In this case, the gradation adjustment (see FIG. 5) performed by the gradation adjustment unit 52 in the present embodiment is an operation of shifting the color of the mucous membrane to light red 86B (marked by ●) and shifting the color of the blood vessel to dark red 87B (marked by ◆). In a case where the color gamut 80 of sRGB in the L*a*b* color space is viewed from the L*=100 (white) side, as shown in FIG. 9, the gradation adjustment performed by the gradation adjustment unit 52 in the present embodiment is, for example, an operation of shifting the color of the mucous membrane and the color of the blood vessel in the "red" direction from the origin point (a*=0 and b*=0). A thick solid line 91 in FIG. 9 is the color gamut of sRGB of L*=70, and a broken line 92 is the color gamut sRGB of L*=60.

Therefore, the color image 57 after the gradation adjustment has a color arrangement substantially similar to that of the white light image as a whole. Since a doctor or the like is accustomed to the color arrangement of the white light image, the color image 57 having a color arrangement close to the white light image is an image that is easy for the doctor or the like to see, as described above.

Further, since the color image 57 is formed by assigning the same specific color image 56 to each of the RGB color channels, the visibility of the subject image shown in the specific color image 56 is not deteriorated.

For example, a generation method of a typical white light image uses white light in broadband to assign a B image obtained by imaging a subject using B pixels to a B channel, to assign a G image obtained by imaging a subject using G pixels to a G channel, and to assign an R image obtained by imaging a subject using R pixels to an R channel. Therefore, even in a case where the surface blood vessel (the blood vessel at a shallow position under the mucous membrane) is shown in the B image, due to the difference in the depth of penetration depending on the wavelength, the surface blood vessel is not shown in the G image and the R image assigned to the G channel and the R channel. Alternatively, even in a case where the surface blood vessel is shown in the G image and the R image, the visibility is usually lower than that of the B image. Therefore, as described above, in the typical white light image, only one color channel (B channel) of the three color channels has information on the surface blood vessel, so that the visibility of the surface blood vessel is lower than that of the original B image.

On the other hand, in the present embodiment, all the three color channels of the color image 57 hold the information contained in the subject image shown in the specific color image 56. Therefore, the features of the subject image that can be visually recognized in the specific color image 56 can be visually recognized in the color image 57 as well.

Figure 10:
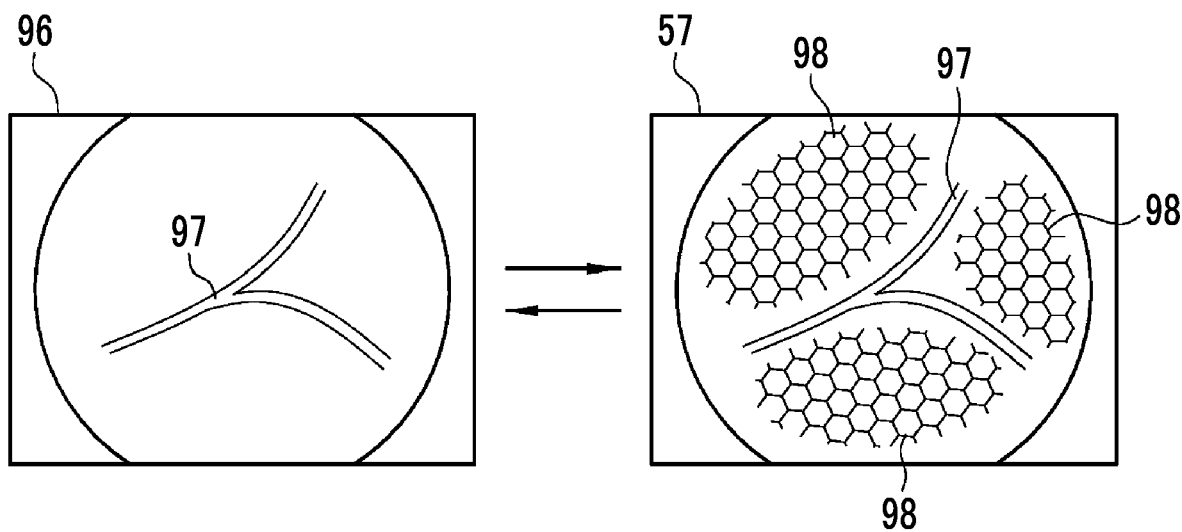
FIG. 10 is an explanatory diagram comparing a white light image and a color image.

As shown in FIG. 10, in a case of comparing a conventional white light image 96 having similar tones with the color image 57 generated by the color image generation unit 12, the white light image 96 and the color image 57 have tones close to each other. Moreover, even in a case where, in the white light image 96, only a relatively thick blood vessel 97 can be visually recognized while a surface blood vessel 98 can be hardly visually recognized, in the color image 57, the surface blood vessel 98 can be clearly observed.

Further, the larger the distance between two points in the L*a*b* color space, the higher the discrimination in consideration of the visual sense. In the present embodiment, the distance between the light red 86B of the mucous membrane and the dark red 87B of the blood vessel in the color image 57 after gradation adjustment is larger than the distance between the light gray 86A of the mucous membrane and the dark gray 87A of the blood vessel in the specific color image 56 (see FIGS. 8 and 9). In this case, the color image 57 has improved discrimination between the mucous membrane and the blood vessel even as compared with the specific color image 56. In this way, by adjusting the distance between two points in the L*a*b* color space to be large in a portion having a higher density than a specific density, which separates the mucous membrane and the blood vessel, and in a portion having a lower density than the specific density, it is possible to generate an image that is easy to see.

In the first embodiment, the specific color image 56 is an image obtained by imaging the subject using narrow-band violet light, but the specific color image 56 may be any image as long as it is an image obtained by imaging the subject using at least monochromatic light. For example, in a case where the image sensor 41 has B pixels, G pixels, and R pixels, the light received by the B pixel, the light received by the G pixel, and the light received by the R pixel are monochromatic lights in relation to the image sensor 41. Therefore, even in a case where broadband light such as white light is used, the B image, the G image, or the R image can be used as the specific color image 56. In a case where a blood vessel or the like that is clearly shown only in the B image is used as a diagnostic material, by using the B image as the specific color image 56, it is possible to generate the color image 57 that maintains the visibility of the blood vessel or the like used as the diagnostic material.

Since it is advantageous in that the color image 57 generated by the color image generation unit 12 can be colorized while maintaining the features (visibility and the like) of the subject image in the specific color image 56 used to generate the color image 57, it is more preferable that the subject image used as a diagnostic material is clearly shown in the specific color image 56. Therefore, as described above, it is preferable that in a case where an image obtained by imaging a subject with monochromatic light is used as the specific color image 56, the "monochromatic light" is any one of violet light, blue light, green light, or red light. The violet light and the blue light used as the monochromatic light can image the tissues such as the surface layer of the mucous membrane or thin blood vessels near the surface layer or the structure such as the pit pattern more clearly than light in other wavelength bands. In a case where green light is used as the monochromatic light, it is possible to image medium-thick blood vessels at a relatively deep position from the surface of the mucous membrane, such as a middle layer of the mucous membrane, more clearly than light in other wavelength bands. Further, in a case where red light is used as the monochromatic light, it is possible to image thick blood vessels and the like at a deep position from the surface of the mucous membrane, such as a deep layer of the mucous membrane. In particular, in the diagnosis using an endoscopic image, since the appearance of blood vessels in the surface layer or the middle-deep layer of the mucous membrane is often used as one of the diagnostic materials, the specific color image 56 is particularly preferably an image captured using violet light, blue light, or green light.

Figure 11:
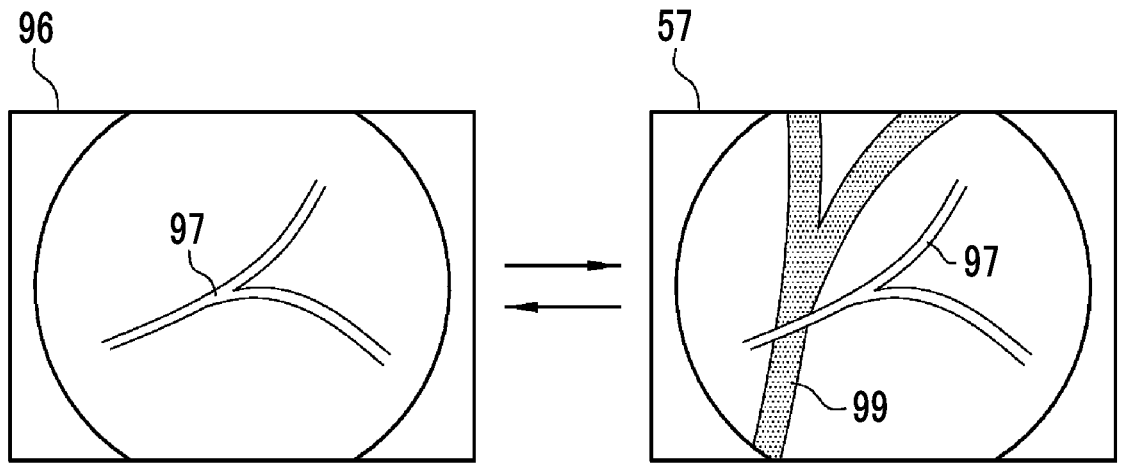
FIG. 11 is an explanatory diagram comparing the white light image and the color image.

Furthermore, the specific color image 56 is preferably an image captured using narrow-band light. This is because the above-described features of the subject image become clearer. That is, the specific color image 56 is preferably an image obtained by imaging the subject using any one of narrow-band violet light, narrow-band blue light, narrow-band green light, or narrow-band red light, and particularly preferably an image obtained by imaging the subject using narrow-band violet light, narrow-band blue light, or narrow-band green light. For example, as shown in FIG. 11, in the conventional white light image 96, a middle-deep blood vessel 99 shown in the G image cannot be observed or is unclear. According to the color image 57 in which the image obtained by imaging the subject using green light (monochromatic light) or narrow-band green light is used as the specific color image 56, the middle-deep blood vessel 99 can be observed as clearly as the G image.

Figure 12:
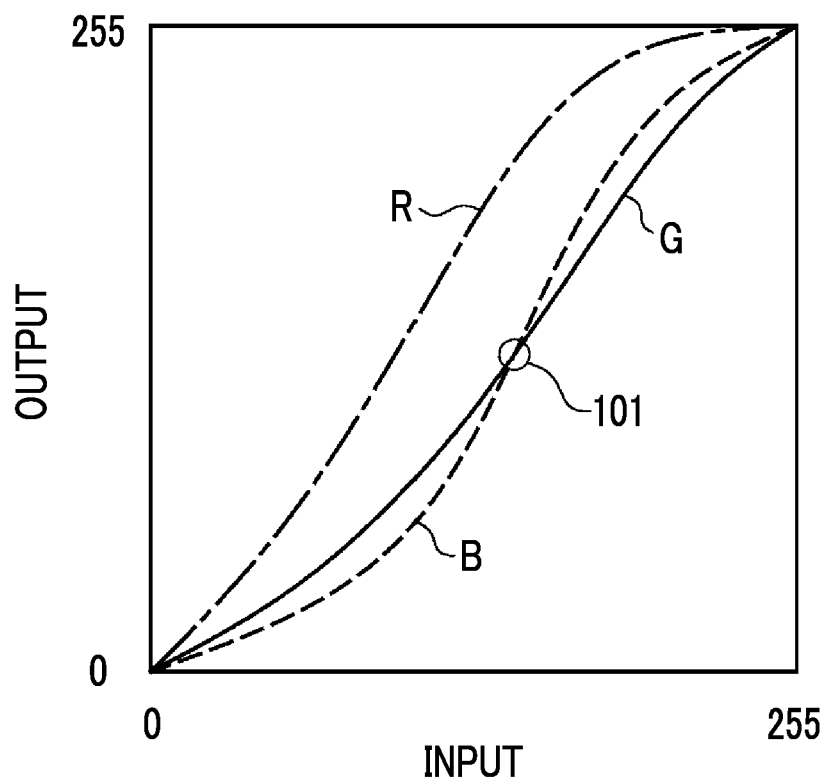
FIG. 12 is a tone curve used for gradation adjustment in a modification example.

In the first embodiment, the gradation adjustment unit 52 uses the tone curve of the balance of B<G<R in almost the entire input/output range to generate the color image 57 having a tone close to that of the white light image; however, the tone curve that can be used by the gradation adjustment unit 52 is not limited thereto, and other types of tone curves can be used. For example, as shown in FIG. 12, by increasing the output of the R channel with respect to at least the B channel and the G channel, the tone of the generated color image 57 as a whole is set to be substantially the same as that of the white light image 96. Then, for example, the tone curves of the B channel and the G channel have an intersection 101, and a balance of B<G is set in a case where the pixel value is smaller than the intersection 101, and a balance of B>G is set in a case where the pixel value is larger than the intersection 101. Consequently, with respect to the intersection 101, the relatively dark pixel becomes more greenish after the gradation adjustment, and the relatively bright pixel becomes more bluish after the gradation adjustment.

Figure 13:
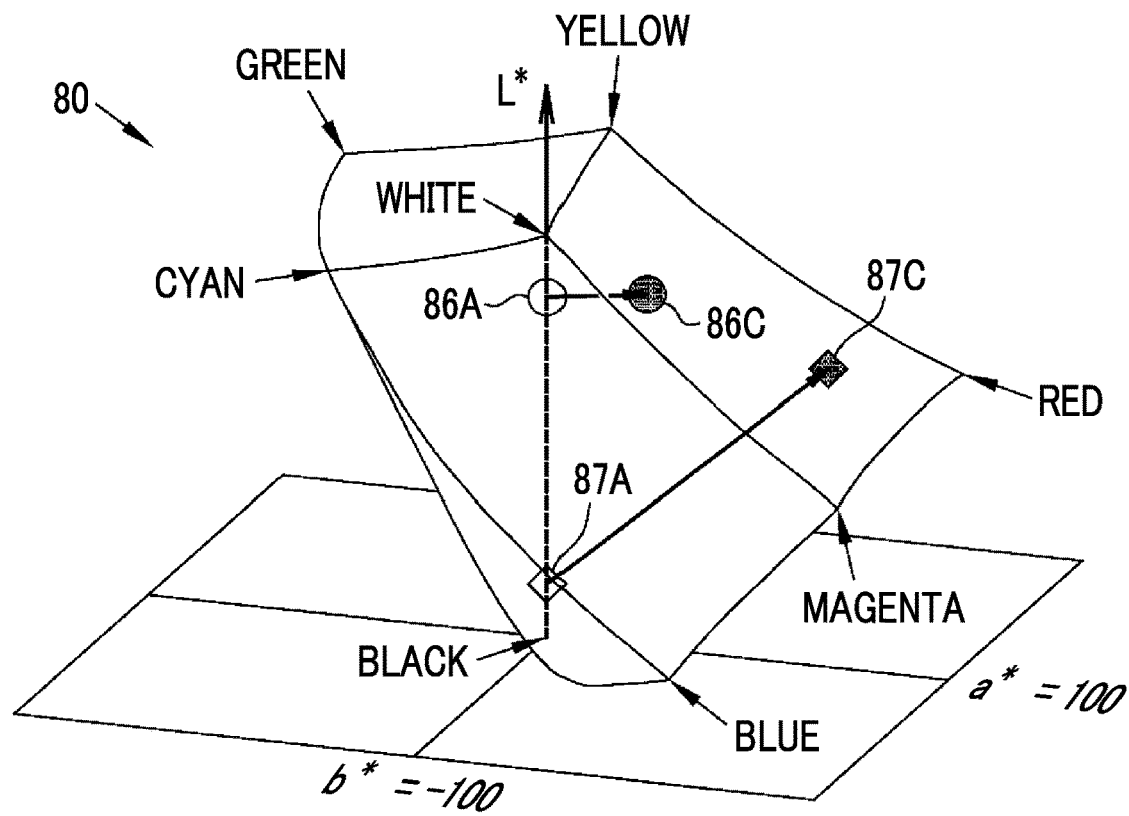
FIG. 13 is an explanatory diagram showing a relationship between gradation adjustment and color change.
Figure 14:
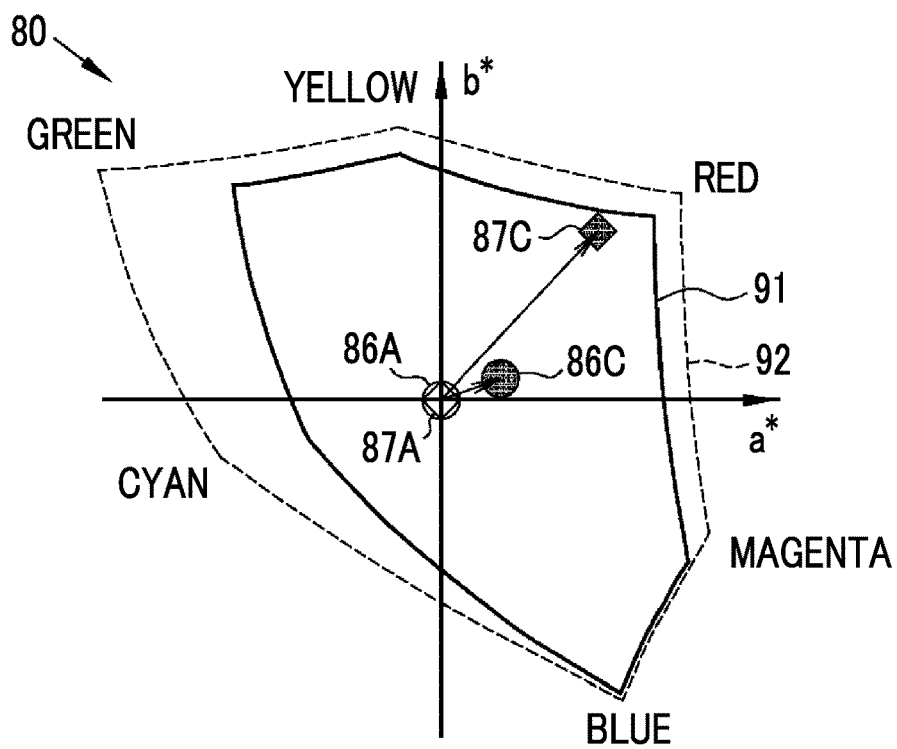
FIG. 14 is an explanatory diagram showing a relationship between the gradation adjustment and the color change.

As shown in FIG. 13, in the color gamut 80, the light gray 86A of the mucous membrane and the dark gray 87A of the blood vessel approach a reddish color as a whole as in the first embodiment. On the other hand, as shown in FIG. 14, the light gray 86A of the mucous membrane shifts to light red 86C which is rotated and moved in the blue direction (clockwise direction) about the L* axis after the gradation adjustment, and the color of the blood vessel shifts to dark red 87C which is rotated and moved in the green direction (counterclockwise direction) about the L* axis after the gradation adjustment, contrary to the color of the mucous membrane. Therefore, in comparison with the light red 86B of the mucous membrane and the dark red 87B of the blood vessel (see FIG. 9 and the like) in a case where the tone curve is set to the balance of B<G<R (see FIG. 5), in a case where each tone curve of the B channel and the G channel has the intersection 101 as described above, the distance between the color of the mucous membrane and the color of the blood vessel after gradation adjustment in the L*a*b* color space is increased. As a result, the relative visibility of the mucous membrane and the blood vessel after gradation adjustment is improved. In this way, with respect to the specific density corresponding to the intersection 101, it is possible to generate an image that is easy to see by adjusting the distance between two points in the L*a*b* color space to be large in the portion having a higher density than the specific density and in the portion having a lower density than the specific density. That is, for example, an image including two observation targets whose visibility is desired to be improved is captured as a specific color image with appropriate brightness by controlling the light amount of specific monochromatic light or narrow-band light. Then, the captured specific color image is assigned to a plurality of color channels, and the color image generation unit 12 performs processing of adjusting the balance of each of the assigned color channels using a tone curve or the like, and generates a color image in which the color distance between two observation targets in the L*a*b* color space is larger than the distance in the specific color image. Thereby, it is possible to generate a color image in which the visibility of the observation target is improved as compared with the specific color image. Note that, the specific density corresponds to the density between the densities of the two observation targets in terms of the density converted from the image including the observation target. The same applies to embodiments described later.

Second Embodiment

Figure 15:
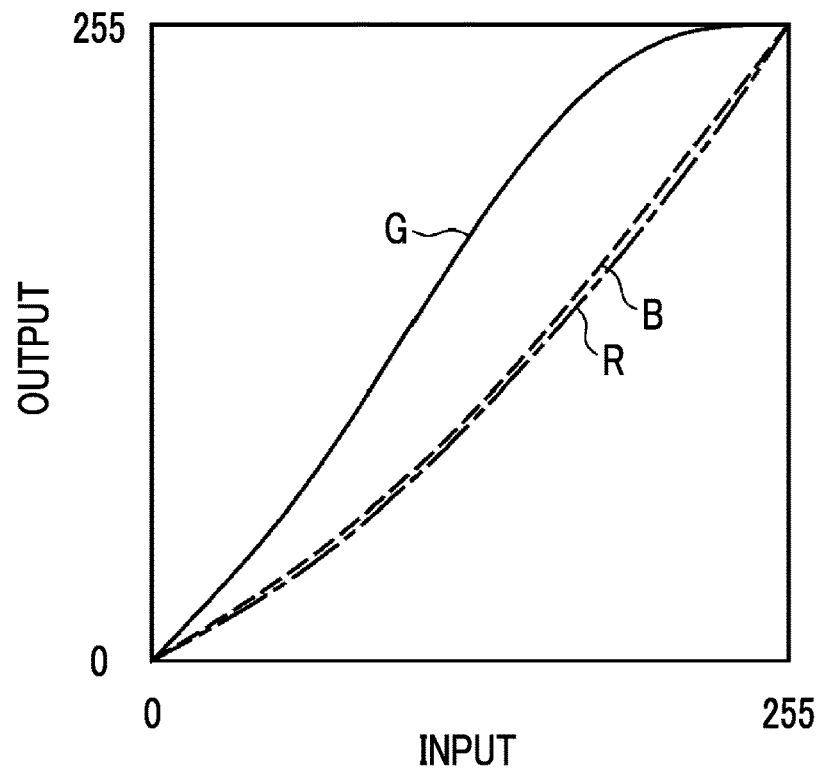
FIG. 15 is a tone curve used for gradation adjustment in a modification example.

In the first embodiment and a modification example, the color image 57 having a color arrangement close to that of the white light image 96 is generated, but the color image generation unit 12 of a second embodiment can generate a color image 57 having a color arrangement different from that of the white light image 96. For example, in a case where the color of the mucous membrane is a greenish color, as shown in FIG. 15, the gradation adjustment unit 52 performs gradation adjustment using a tone curve in which the balance of input and output is R≈B<G in almost the entire input/output range. For example, in the case of an input image having a maximum pixel value of 255, a tone curve in which the pixel value is in the range of 100 to 200 and G is about 1.3 to 2.0 times larger than R and B is preferable.

Figure 16:
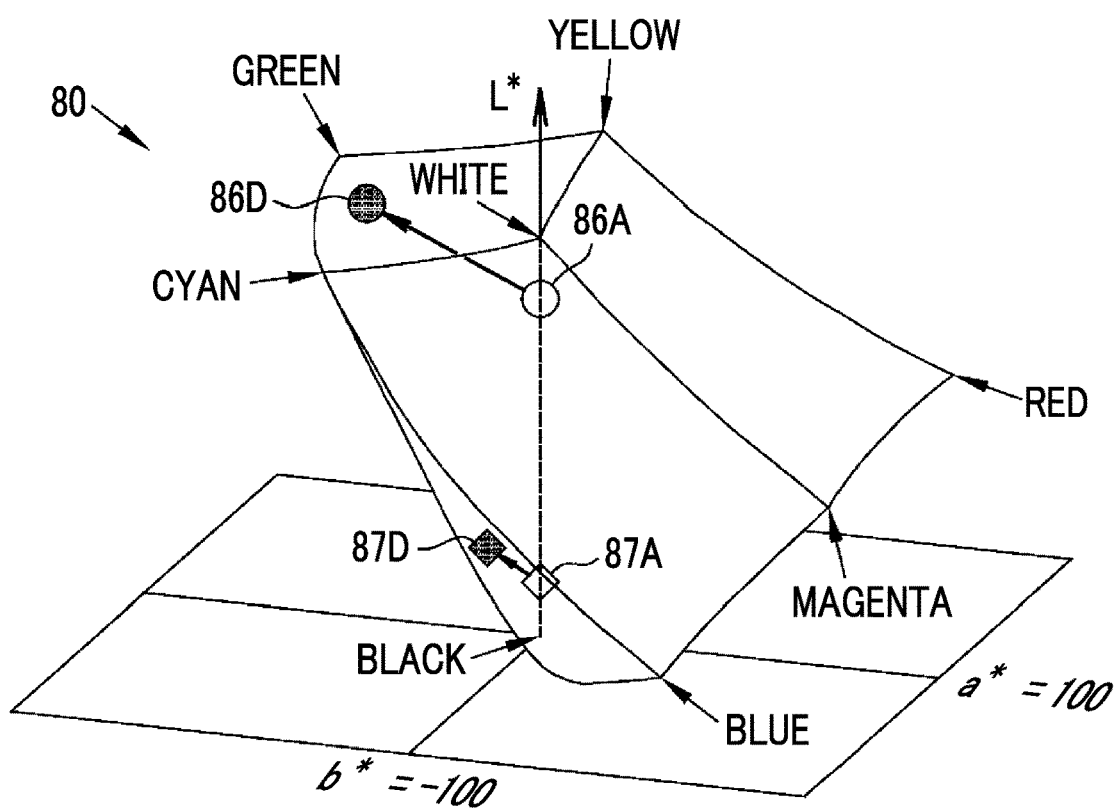
FIG. 16 is an explanatory diagram showing a relationship between gradation adjustment and color change.
Figure 17:
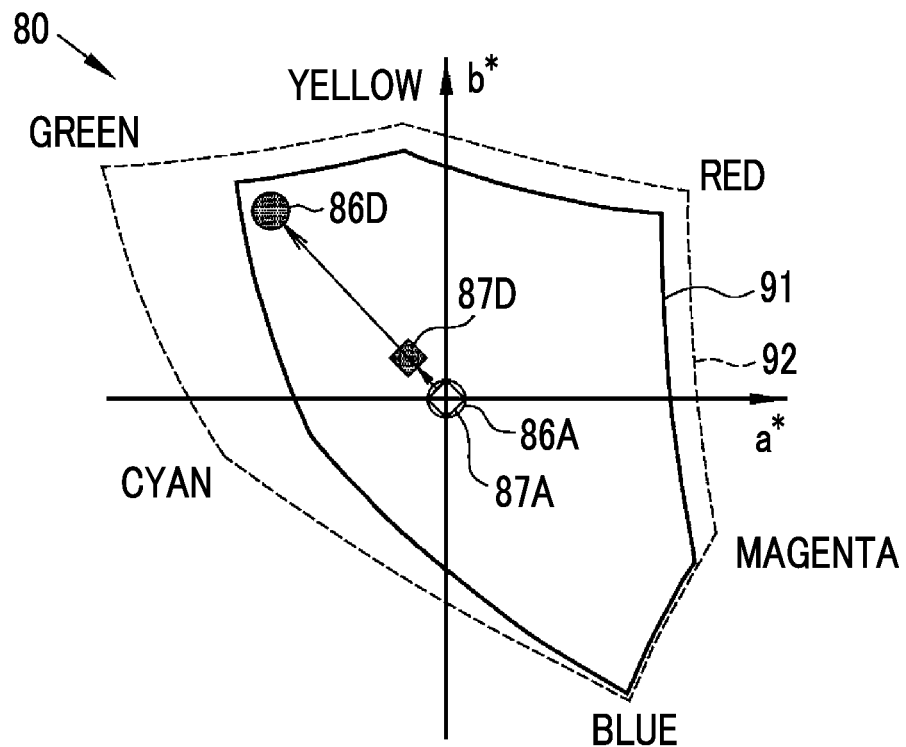
FIG. 17 is an explanatory diagram showing a relationship between gradation adjustment and color change.

In this case, as shown in FIG. 16, in the color gamut 80, the light gray 86A of the mucous membrane in the specific color image 56 shifts to the light green 86D after gradation adjustment, and the dark gray 87A of the blood vessel in the specific color image 56 shifts to the dark green 87D after gradation adjustment. Then, in a case where the color of the mucous membrane is a greenish color, as shown in FIG. 17, the distance between the light green 86D of the mucous membrane and the dark green 87D of the blood vessel after gradation adjustment becomes larger than the distance between the light gray 86A of the mucous membrane and the dark gray 87A of the blood vessel in the specific color image 56, and at least the same distance as the distance between the light gray 86A of the mucous membrane and the dark gray 87A of the blood vessel in the specific color image 56 can be maintained. Therefore, in a case where gradation adjustment is performed using a tone curve set to a balance of R≈B<G, the relative visibility of the mucous membrane and the blood vessel can be improved. In particular, as can be seen from the difference in the color gamut of sRGB having different lightness (values of L*) indicated by the thick solid line 91 and the broken line 92, the greenish color has also an advantage that the color image 57 as a whole is bright because it is easy to keep the distance from the origin point (a*=0 and b*=0) even in a case where the lightness is high. The entirely bright color image 57 is easier to discriminate the mucous membrane and the blood vessel than the entirely dark color image 57.

Figure 18:
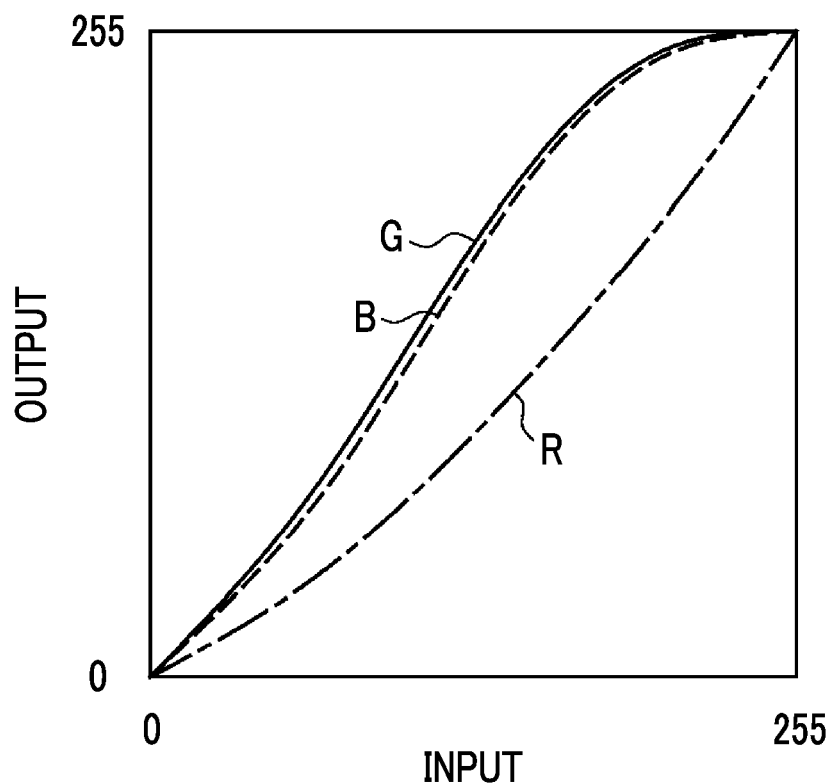
FIG. 18 is a tone curve used for gradation adjustment in a modification example.

Note that, as shown in FIG. 18, the gradation adjustment unit 52 can adjust the gradation of the color image 57 by using a tone curve set to a balance of R<B≈G. In this case, the color image 57 becomes a cyanish color. By adjusting the balance of the tone curve for each of the RGB color channels, the entire color image 57 can be made yellowish, magentaish, or bluish. In order to improve the relative visibility of the mucous membrane and the blood vessel, it is better that the mucous membrane is bright, on the contrary, the blood vessel is dark, and the distance between the colors of the mucous membrane and the blood vessel in the L*a*b* color space is large. Therefore, in order to maintain the brightness of the mucous membrane and the color image 57 as a whole, it is preferable to use a bright color (a color that can be displayed in a case where the lightness (L*) is large). Specifically, it is desirable to employ a tone curve for coloring the mucous membrane and the entire color image 57 with a greenish color, a yellowish color, a magentaish color, or a cyanish color that can be expressed even in a case where L*=80 or more. Most preferably, the colors of the mucous membrane and the entire color image 57 are a greenish color that can express from a bright color to a dark color. For example, it is preferable that in a case where the subject image includes a mucous membrane, the color of at least the mucous membrane is a greenish color such as green.

Third Embodiment

In the first embodiment, the second embodiment, and the modification examples thereof, the color image generation unit 12 uses the gradation adjustment unit 52 to adjust the gradation of the color image 57 to be generated by the tone curve; however, the color image generation unit 12 or the gradation adjustment unit 52 of a third embodiment can perform gradation adjustment using a gain instead of or in combination with the gradation adjustment using the tone curve. That is, the color image generation unit 12 or the gradation adjustment unit 52 can adjust the gain applied to the specific color image 56 in a case where the specific color image 56 is assigned to the color channels.

Figure 19:
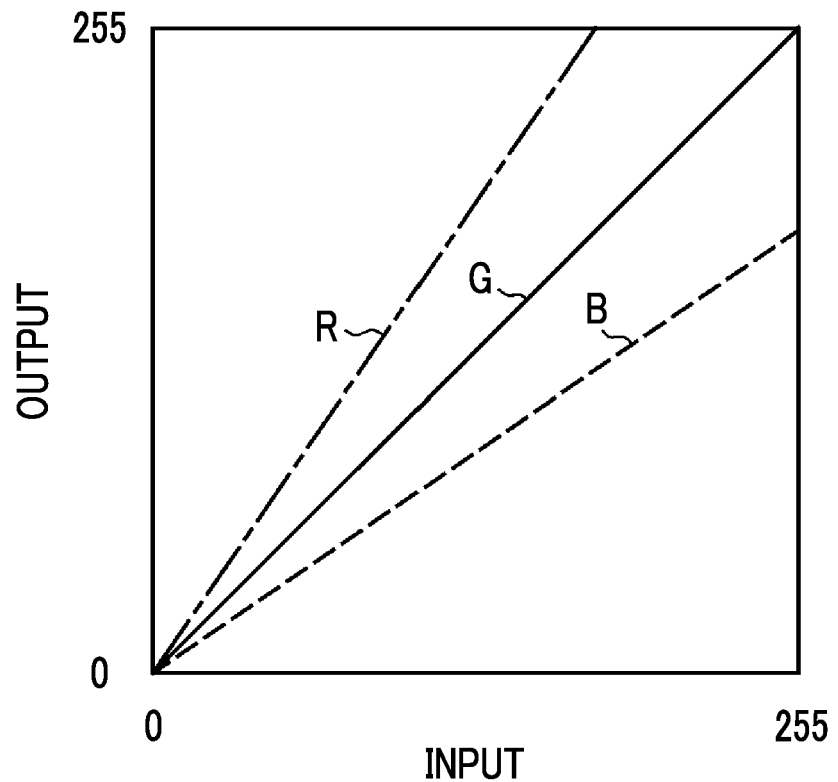
FIG. 19 is a graph showing contents of gradation adjustment using a gain of a third embodiment.

As shown in FIG. 19, gradation adjustment in which the R channel is multiplied by a gain larger than "1", the G channel is multiplied by a gain "1", and the B channel is multiplied by a gain smaller than "1" shows a similar operation effect to the gradation adjustment of the color image 57 using the tone curve having a balance of B<G<R (see FIG. 5). In a case where the gradation adjustment using the tone curve and the gradation adjustment by the gain are combined, finer gradation adjustment can be performed as compared with the present embodiment and the first and second embodiments.

In the third embodiment, the color image generation unit 12 or the gradation adjustment unit 52 multiplies each of the RGB color channels by a gain, but the color image generation unit 12 or the gradation adjustment unit 52 can apply a gain to each of the RGB color channels of the color image 57 in any manner such as adding, subtracting, or dividing the gain to each of the RGB color channels of the color image 57. That is, "applying" a gain to each of the RGB color channels of the color image 57 means performing any calculation using the gain on each of the RGB color channels of the color image 57. Further, as in the third embodiment, gains having different values can be applied to the RGB color channels, respectively. In a case where gradation adjustment is performed only by a gain, it is preferable to apply a gain different from that of the other color channels to at least one color channel of each of the RGB color channels.

Fourth Embodiment

In the first embodiment, the second embodiment, the third embodiment, and the modification examples thereof, the color image generation unit 12 or the gradation adjustment unit 52 performs uniform gradation adjustment for each color channel of the color image 57, but the color image generation unit 12 of a fourth embodiment can change the balance of the color channels for each pixel or for each region including a plurality of pixels.

Figure 20:
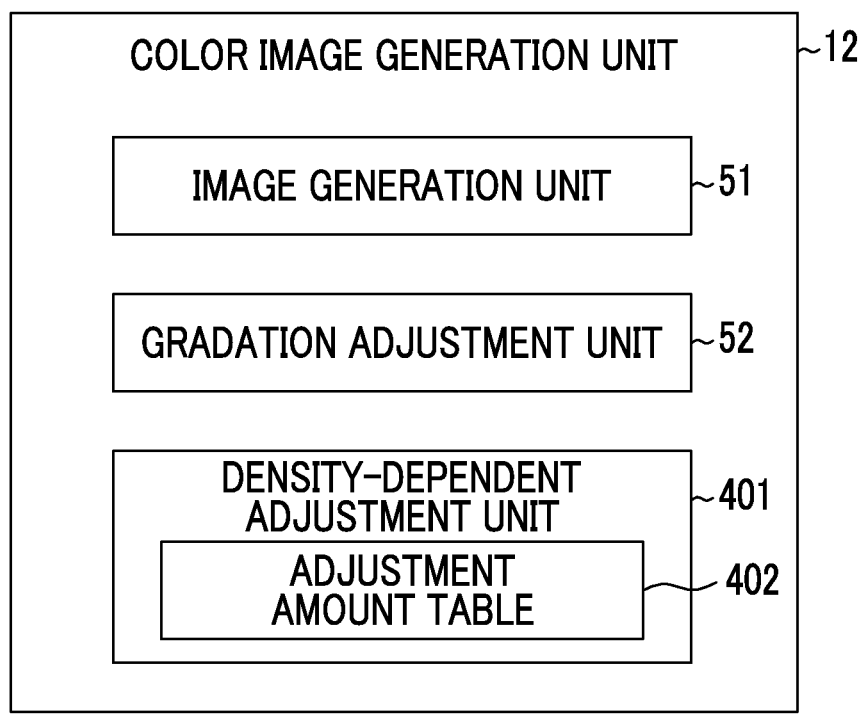
FIG. 20 is a block diagram showing a configuration of a color image generation unit of a fourth embodiment.

In the present embodiment, the color image generation unit 12 adjusts the balance of the color channel for each pixel depending on the density of the subject image. In this case, as shown in FIG. 20, the color image generation unit 12 comprises a density-dependent adjustment unit 401 in addition to the image generation unit 51 and the gradation adjustment unit 52. The density-dependent adjustment unit 401 further adjusts the balance of the color channels using a density of the subject image with respect to the color image 57 whose gradation adjustment has been performed by the gradation adjustment unit 52. The density-dependent adjustment unit 401 also comprises an adjustment amount table 402 that associates the density of the subject image with the adjustment amount.

The "density of the subject image" is the density of the subject image in the color image 57 or the specific color image 56 after gradation adjustment. In the subject image, the bright portion has a low density and the dark portion has a high density. In the present embodiment, the density of the subject image is determined using brightness "Y1" of the color image 57 after the gradation adjustment. In a case where the value of the R channel in a certain pixel of the color image 57 after gradation adjustment is R1, the value of the G channel of the same pixel is G1, and the value of the B channel of the same pixel is B1, the brightness Y1 of the same pixel is, for example, $Y1=0.3 \times R1+0.6 \times G1+0.1 \times B1$. Then, in the color image 57 after the gradation adjustment, in a case where the brightness at a certain pixel is "Y1", the density of the subject image at this pixel is represented by "1/Y1" here.

Figure 21:
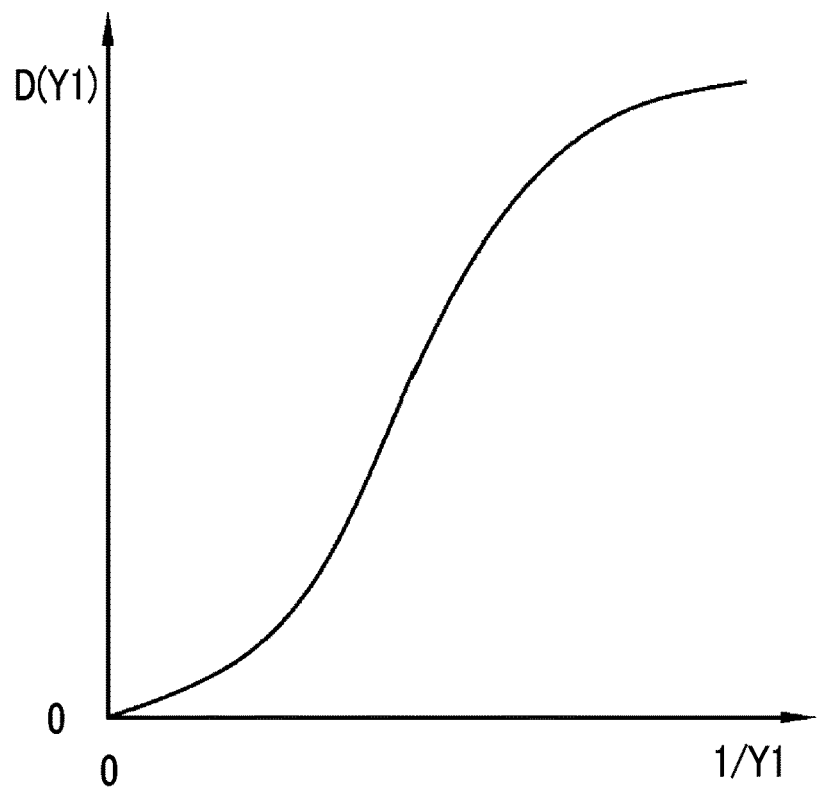
FIG. 21 is a graph showing a relationship between a density of a subject image and an adjustment amount.

More specifically, as shown in FIG. 21, the adjustment amount table 402 associates the density "1/Y1" of the subject image with an adjustment amount D(Y1) according to a specific function or the like. In the present embodiment, the higher the density "1/Y1" of the subject image, the larger the adjustment amount D(Y1).

In a case where the value of the R channel in the same pixel after the density-dependent adjustment is R2, the value of the G channel in the same pixel after the density-dependent adjustment is G2, and the value of the B channel in the same pixel after the density-dependent adjustment is B2, which are performed by the density-dependent adjustment unit 401, the density-dependent adjustment unit 401 uses the following equations (1) to (3) to perform the adjustment depending on the density of the subject image. In equations (1) to (3), a coefficient α is the intensity of density-dependent adjustment.

$$R2=R1\pm\alpha\times D(Y1) \quad (1)$$

$$G2=G1\pm\alpha\times D(Y1) \quad (2)$$

$$B2=B1\pm\alpha\times D(Y1) \quad (3)$$

The sign (±) of an adjustment term "α×D(Y1)" related to the density-dependent adjustment is independently set for each of the equations (1) to (3) according to the content of the gradation adjustment in the gradation adjustment unit 52. For example, in a case where the color image 57 after gradation adjustment is the color image 57 in which gradation is adjusted so that the mucous membrane is greenish (in a case where it is the color image 57 in the second embodiment), the sign of the adjustment term in the R channel is positive, the sign of the adjustment term in the G channel is negative, and the sign of the adjustment term in the B channel is positive. That is, the density-dependent adjustment unit 401 uses the following equations (4) to (6) to perform the adjustment depending on the density of the subject image.

$$R2=R1+\alpha\times D(Y1) \quad (4)$$

$$G2=G1-\alpha\times D(Y1) \quad (5)$$

$$B2=B1+\alpha\times D(Y1) \quad (6)$$

According to the equations (4) to (6), in a case where the subject image has a high density, the values of the R channel (R2) and the B channel (B2) after the density-dependent adjustment are larger than that of the color image 57 after the gradation adjustment, and the value of the G channel (G2) after the density-dependent adjustment is smaller than that of the color image 57 after the gradation adjustment. Further, as the density of the subject image is higher, the color of the pixel shifts to the color in the positive direction of substantially a* in the L*a*b* color space. On the other hand, the lower the density of the subject image is, the smaller the value of the adjustment amount D(Y1) is, and therefore the change in the color of the color image 57 after gradation adjustment is small.

Figure 22:
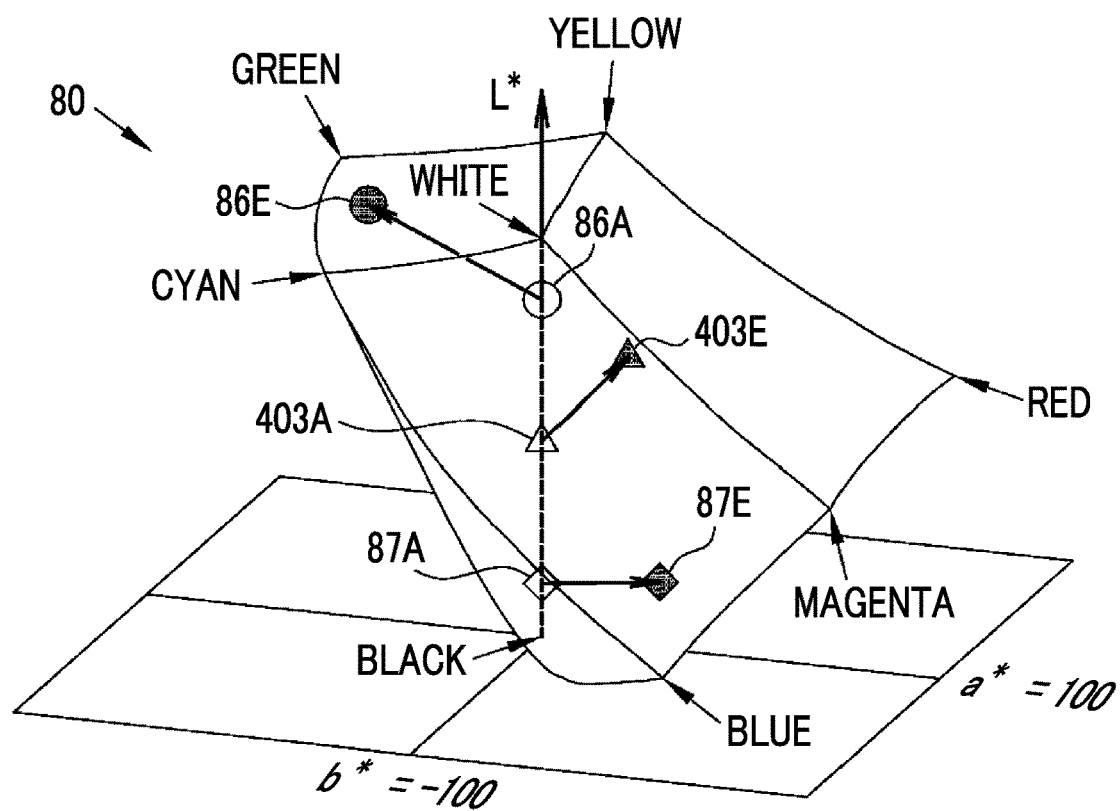
FIG. 22 is an explanatory diagram showing a relationship between density-dependent adjustment and color change.
Figure 23:
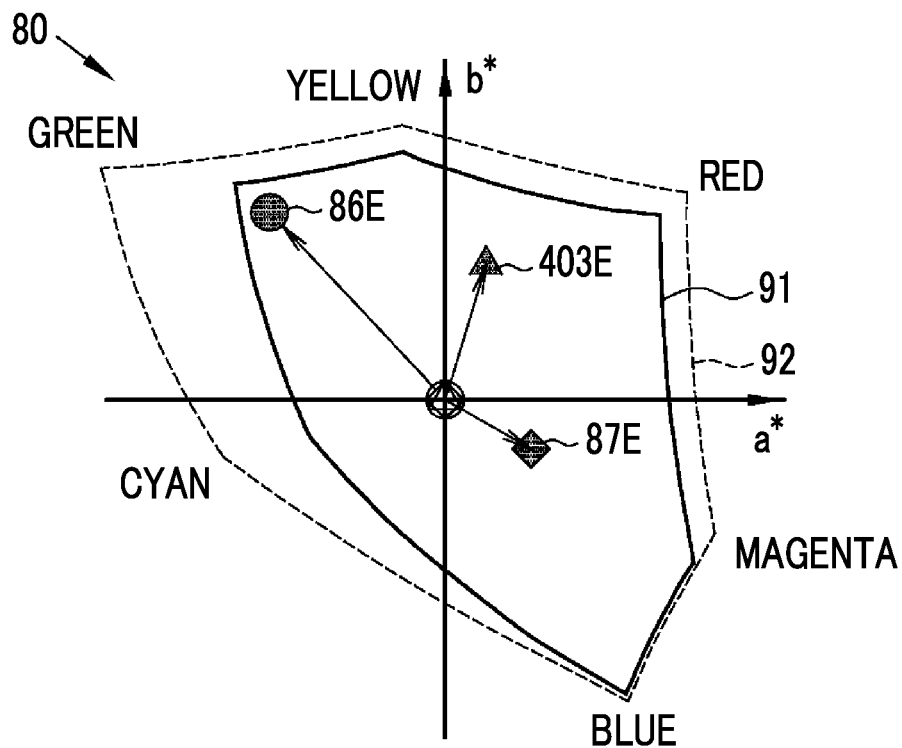
FIG. 23 is an explanatory diagram showing a relationship between density-dependent adjustment and color change.

Therefore, for example, in the mucous membrane portion of the subject image, the lightness is high and the density of the subject image is low, so that as shown in FIGS. 22 and 23, in the color gamut 80 of the L*a*b* color space, the color (light green 86E) of the mucous membrane after the density-dependent adjustment is almost the same as the color (light green 86D (see FIG. 17)) of the mucous membrane after the gradation adjustment. On the other hand, in the blood vessel portion of the subject image, the lightness is low and the density of the subject image is high, so that in the color gamut 80 of the L*a*b* color space, the color of the blood vessel largely changes from the color (dark green 87D (see FIG. 17)) of the blood vessel after the density-dependent adjustment and becomes, for example, dark magenta 87E. Further, in the specific color image 56, gray 403 of the tissue having the brightness between the mucous membrane and the blood vessel becomes, for example, orange 403E after the density-dependent adjustment. In this way, the colors of the mucous membrane and the blood vessel after the density-dependent adjustment are expanded in the color gamut 80. As a result, the relative discrimination between the mucous membrane and the blood vessel is improved. In this way, with respect to the specific density corresponding to the intersection 101, it is possible to generate an image that is easy to see by adjusting the distance between two points in the L*a*b* color space to be large in the portion having a higher density than the specific density and in the portion having a lower density than the specific density.

As described above, in the present embodiment, the color image generation unit 12 uses the density-dependent adjustment unit 401 to increase the distance between the color of the portion of the subject image having a relatively lower density than the specific density and the color of the portion of the subject image having a relatively higher density than the specific density, in the L*a*b* color space. Therefore, it is possible to improve the relative discrimination between the low density portion and the high density portion in the subject image.

Further, the coefficient α represents the amount of color shift in the color gamut 80, and the combination of signs of the adjustment terms represents the color shift direction in the color gamut 80. For example, it is preferable that, depending on the magnitude of the coefficient α and the combination of signs of the adjustment terms, the targets to be relatively discriminated in the diagnosis (for example, mucous membrane and blood vessel) have opposite colors (complementary colors) in the color gamut 80 after the density-dependent adjustment. In the present embodiment, the color of the mucous membrane after the density-dependent adjustment is the light green 86E, and the color of the blood vessel after the density-dependent adjustment is dark magenta 87E. Therefore, the relative discrimination between the mucous membrane and the blood vessel is further improved by the density-dependent adjustment.

In a case where the color image 57 after gradation adjustment has a tone close to that of the white light image 96 (in a case where it is the color image 57 in the first embodiment), for example, the sign of the adjustment term in the R channel is positive, the sign of the adjustment term in the G channel is negative, and the sign of the adjustment term in the B channel is negative. That is, the density-dependent adjustment unit 401 uses the following equations (7) to (9) to perform the adjustment depending on the density of the subject image.

$$R2=R1+\alpha\times D(Y1) \quad (7)$$

$$G2=G1-\alpha\times D(Y1) \quad (8)$$

$$B2=B1-\alpha\times D(Y1) \quad (9)$$

In a case where the color image 57 after gradation adjustment has a tone close to that of the white light image 96, when the combination of the signs of the adjustment terms is set as described above, the mucous membrane portion having a low density approaches the L* axis (light gray 86A) after density-dependent adjustment and the blood vessel portion having a high density becomes more reddish while maintaining the tone close to that of the white light image 96 as a whole. Therefore, the relative discrimination between the mucous membrane and the blood vessel is improved as compared with the case where the density-dependent adjustment is not performed.

In the fourth embodiment, the coefficient α of the adjustment term is common to each of the RGB color channels, but the coefficient α of the adjustment term may use a different value for each of the RGB color channels. Further, in the fourth embodiment, the adjustment amount D(Y1) is common to each of the RGB color channels, but the adjustment amount D(Y1) may use a different value for each of the RGB color channels. In this case, different adjustment amount tables are used for the respective color channels. For example, instead of the adjustment amount table 402, an adjustment amount table for the R channel, an adjustment amount table for the G channel, and an adjustment amount table for the B channel are used.

Further, in the fourth embodiment, the adjustment amount D(Y1) depending on the density of the subject image is added to or subtracted from the value of each of the RGB color channels of the color image 57 after gradation adjustment. However, the adjustment depending on the density of the subject image using the adjustment amount D(Y1) may be performed by other calculations on the value of each of the RGB color channels of the color image 57 after gradation adjustment, for example, multiplying by the adjustment amount D(Y1), dividing by the adjustment amount D(Y1), or a combination of four operations and/or any other calculation mode.

Fifth Embodiment

Figure 24:
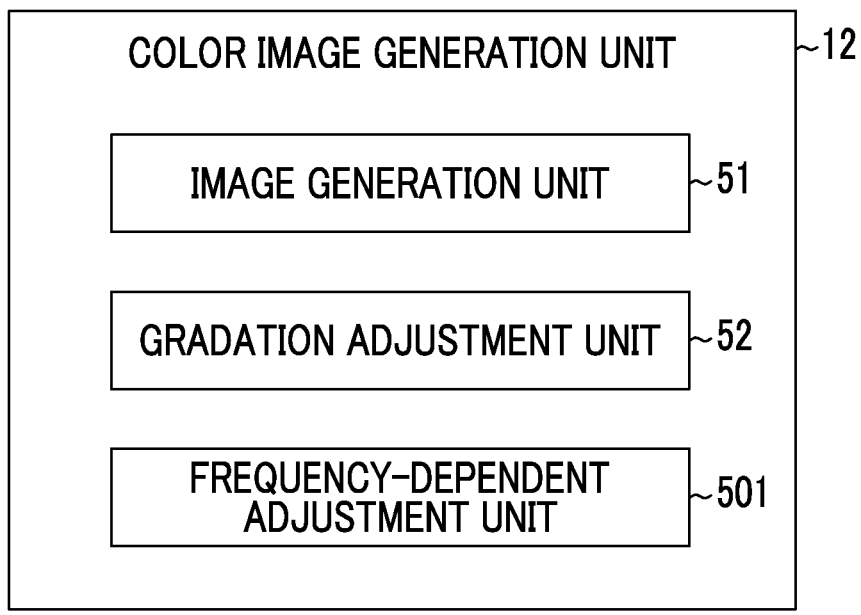
FIG. 24 is a block diagram showing a configuration of a color image generation unit of a fifth embodiment.

In the fourth embodiment, the color image generation unit 12 adjusts the balance of the color channels for each pixel depending on the density of the subject image, but the color image generation unit 12 of a fifth embodiment can adjust the balance of the color channels for each pixel or for each region including a plurality of pixels depending on the frequency of the subject image. In this case, as shown in FIG. 24, the color image generation unit 12 comprises a frequency-dependent adjustment unit 501 in addition to the image generation unit 51 and the gradation adjustment unit 52.

The frequency-dependent adjustment unit 501 further adjusts the balance of the color channels using a frequency of the subject image with respect to the color image 57 whose gradation adjustment has been performed by the gradation adjustment unit 52. More specifically, the frequency-dependent adjustment unit 501 acquires an image (hereinafter, referred to as a brightness image) that represents brightness Y0 of the specific color image 56 or the brightness Y1 of the color image 57 after gradation adjustment. Then, a specific frequency component image is obtained by extracting a specific frequency component from the brightness image.

Figure 25:
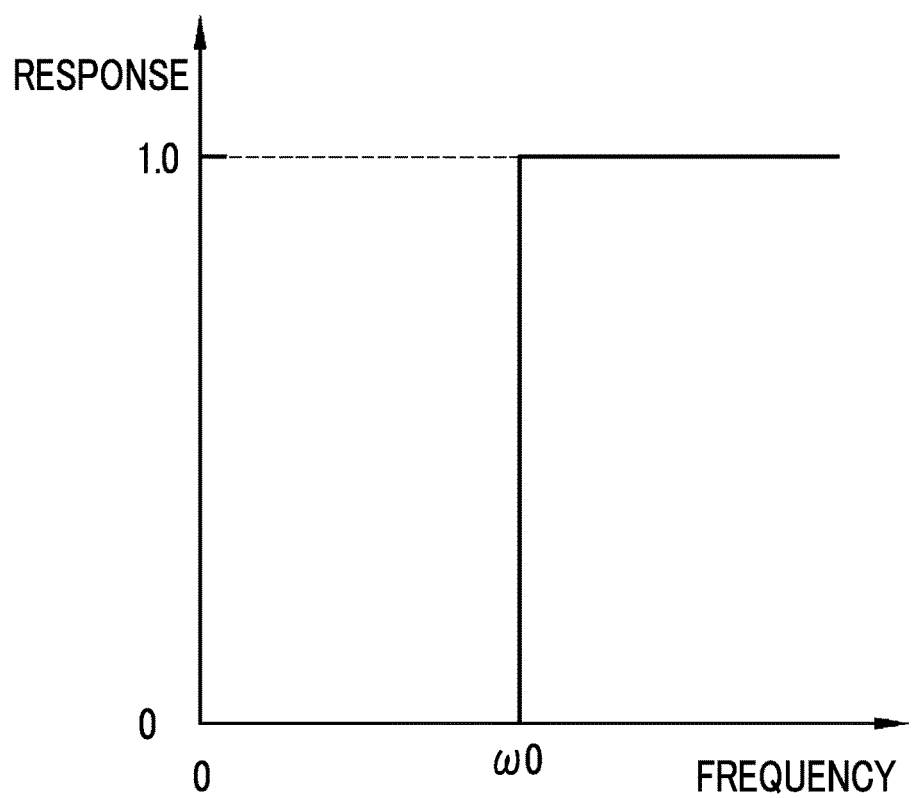
FIG. 25 is a graph showing a range of a frequency extracted from a subject image.

In the present embodiment, the frequency-dependent adjustment unit 501 acquires a brightness image (hereinafter, referred to as a Y1 image) that represents the brightness Y1 of the color image 57 after gradation adjustment. Then, as shown in FIG. 25, the frequency-dependent adjustment unit 501 extracts, for example, a subject image having a frequency component equal to or higher than a specific frequency ω0 from the Y1 image. Thereby, the frequency-dependent adjustment unit 501 obtains a high frequency component image of the Y1 image as the specific frequency component image.

The frequency-dependent adjustment unit 501 uses the specific frequency component image to perform gradation adjustment on the gradation-adjusted color image 57 according to the frequency of the subject image. Specifically, in a case where the value of the R channel in a certain pixel after the frequency-dependent adjustment is R3, the value of the G channel in the same pixel after the frequency-dependent adjustment is G3, and the value of the B channel in the same pixel after the frequency-dependent adjustment is B3, gradation adjustment is performed using the following equations (10) to (12). F(Y1) is the pixel value (brightness) of the same pixel in the specific frequency component image, and a coefficient β is the intensity of frequency-dependent adjustment. Further, the sign (±) of an adjustment term "F(Y1)×β" is independently set for each of the equations (10) to (12) according to the content of the gradation adjustment in the gradation adjustment unit 52.

$$R3 = R1 \pm F(Y1) \times \beta \tag{10}$$

$$G3 = G1 \pm F(Y1) \times \beta \tag{11}$$

$$B3 = B1 \pm F(Y1) \times \beta \tag{12}$$

In a case where the color image 57 after gradation adjustment is the color image 57 in which gradation is adjusted so that the mucous membrane is greenish (in a case where it is the color image 57 in the second embodiment), and in a case where the high frequency component image of the Y1 image is obtained as the specific frequency component image, the sign of the adjustment term in the R channel is positive, the sign of the adjustment term in the G channel is negative, and the sign of the adjustment term in the B channel is positive, for example. That is, the frequency-dependent adjustment unit 501 uses the following equations (13) to (15) to perform the adjustment depending on the density of the subject image.

$$R3 = R1 + F(Y1) \times \beta \tag{13}$$

$$G3 = G1 - F(Y1) \times \beta \tag{14}$$

$$B3 = B1 + F(Y1) \times \beta \tag{15}$$

According to the equations (13) to (15), for a high frequency component equal to or higher than the frequency ω0 in the subject image, the values of the R channel (R3) and the B channel (B3) after the frequency-dependent adjustment are larger than that of the color image 57 after the gradation adjustment, and the value of the G channel (G3) is smaller than that of the color image 57 after the gradation adjustment. On the other hand, for a low frequency component (component whose frequency is smaller than ω0) in the subject image, even after frequency-dependent adjustment, the value of each of the color channels is equal to that of the color image 57 after the gradation adjustment.

For example, in the subject image, the image of the mucous membrane has a low frequency component and the image of the blood vessel has a high frequency component. Therefore, in a case where the frequency-dependent adjustment is performed as described above, the color of the mucous membrane maintains the color of the mucous membrane after gradation adjustment (see light green 86D (FIG. 17)), while the color of the blood vessel becomes, for example, dark magenta. In this way, the distance between the colors of the mucous membrane and the blood vessel after the frequency-dependent adjustment is increased in the color gamut 80. As a result, the relative discrimination between the mucous membrane and the blood vessel is improved.

As described above, in the present embodiment, the color image generation unit 12 comprises the frequency-dependent adjustment unit 501 to increase the distance between the color of the component of the subject image having a relatively lower frequency than the specific frequency and the color of the component of the subject image having a relatively higher frequency than the specific frequency, in the L*a*b* color space. Therefore, it is possible to improve the relative discrimination between the low frequency component and the high frequency component in the subject image.

Further, the coefficient β represents the amount of color shift in the color gamut 80, and the combination of signs of the adjustment terms represents the color shift direction in the color gamut 80. For example, it is preferable that, depending on the magnitude of the coefficient β and the combination of signs of the adjustment terms, the targets to be relatively discriminated in the diagnosis (for example, mucous membrane and blood vessel) have opposite colors (complementary colors) in the color gamut 80 after the frequency-dependent adjustment. In the present embodiment, the color of the mucous membrane after the frequency-dependent adjustment is the light green 86D, and the color of the blood vessel after the frequency-dependent adjustment is dark magenta. Therefore, the relative discrimination between the mucous membrane and the blood vessel is particularly improved by the frequency-dependent adjustment.

In a case where the color image 57 after gradation adjustment has a tone close to that of the white light image 96 (in a case where it is the color image 57 in the first embodiment), for example, the sign of the adjustment term in the R channel is positive, the sign of the adjustment term in the G channel is negative, and the sign of the adjustment term in the B channel is negative. That is, the frequency-dependent adjustment unit 501 uses the following equations (16) to (18) to perform the adjustment depending on the density of the subject image.

$$R3 = R1 + F(Y1) \times \beta \quad (16)$$

$$G3 = G1 - F(Y1) \times \beta \quad (17)$$

$$B3 = B1 - F(Y1) \times \beta \quad (18)$$

In a case where the color image 57 after gradation adjustment has a tone close to that of the white light image 96, when the combination of the signs of the adjustment terms is set as described above, the mucous membrane portion having a low frequency component maintains the color of the color image 57 after gradation adjustment and the blood vessel portion having a high frequency component becomes more reddish while maintaining the tone close to that of the white light image 96 as a whole. Therefore, the relative discrimination between the mucous membrane and the blood vessel is improved as compared with the case where the frequency-dependent adjustment is not performed.

In the fifth embodiment, the coefficient β of the adjustment term is common to each of the RGB color channels, but the coefficient β of the adjustment term may use a different value for each of the RGB color channels.

Figure 26:
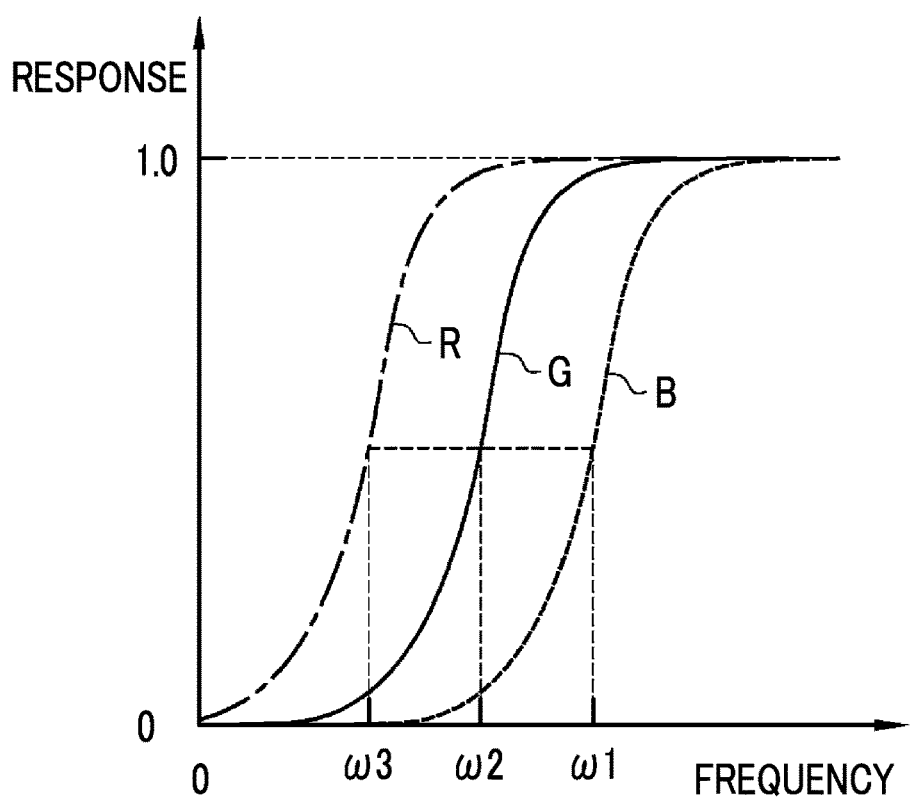
FIG. 26 is a graph showing a range of frequencies extracted from the subject image in a modification example.

In the fifth embodiment, the specific frequency ω0 is set on the assumption that the specific color image 56 obtained by imaging a subject using narrow-band violet light is used. However, the value of the specific frequency can be changed according to the property (imaging condition) of the specific color image 56. For example, as shown in FIG. 26, in a case where the specific color image 56 is an image captured using violet light, blue light, or other light of a relatively short wavelength (indicated by the sign "B" in FIG. 26), the specific frequency can be set to "ω1", in a case where the specific color image 56 is an image captured using light of a medium wavelength such as green light (indicated by the sign "G" in FIG. 26), the specific frequency can be set to "ω2" (ω2<ω1), and in a case where the specific color image 56 is an image captured using light of a long wavelength such as red light (indicated by the sign "R" in FIG. 26), the specific frequency can be set to "ω3" (ω3<ω2). In this way, in a case where the specific frequency is set to be larger as the wavelength of the light used to capture the specific color image 56 is shorter, the relative discrimination between the mucous membrane and the blood vessel can be adequately improved. This is because the shorter the wavelength of the light used to capture the specific color image 56, the easier it is to capture the thin blood vessels that are high frequency components in the subject image, and the longer the wavelength of the light used to capture the specific color image 56, the easier it is to capture the thick blood vessels closer to the low frequency component in the subject image.

In the fifth embodiment, the frequency-dependent adjustment is performed using the high frequency component image of the Y1 image representing the subject image having the frequency component equal to or higher than the specific frequency ω0, but the specific frequency can be set within a predetermined range. For example, an image (specific frequency range image) obtained by extracting components having a frequency ω4 or higher and a frequency ω5 or lower from the Y1 image can be used as the adjustment term of the frequency-dependent adjustment.

In the fifth embodiment, the frequency-dependent adjustment is performed using the specific frequency component image. However, as in the case of the density-dependent adjustment of the fourth embodiment, a numerical value table (adjustment amount table) representing the frequency-dependent adjustment amount may be prepared in advance, and the adjustment term for the frequency-dependent adjustment may be determined using the numerical value table. In this case, different adjustment amount tables may be used for the respective color channels. For example, instead of the adjustment amount table 402, an adjustment amount table for the R channel, an adjustment amount table for the G channel, and an adjustment amount table for the B channel can be used.

Sixth Embodiment

In the fourth embodiment, the density-dependent adjustment that depends on the density of the subject image is performed, and in the fifth embodiment, the frequency-dependent adjustment that depends on the frequency of the subject image is performed, but these can be performed in combination. That is, the color image generation unit 12 of the sixth embodiment can simultaneously perform density-dependent adjustment and frequency-dependent adjustment.

Figure 27:
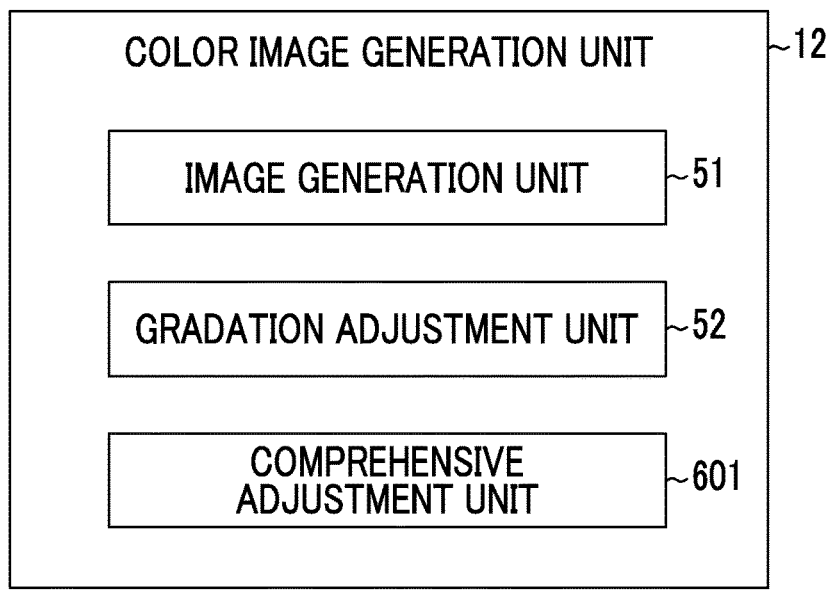
FIG. 27 is a block diagram showing a configuration of a color image generation unit of a sixth embodiment.

In this case, as shown in FIG. 27, the color image generation unit 12 comprises a comprehensive adjustment unit 601 in addition to the image generation unit 51 and the gradation adjustment unit 52. The comprehensive adjustment unit 601 adjusts the balance of the color channels by using the density and frequency of the subject image. The comprehensive adjustment unit 601 determines the density-dependent adjustment amount D(Y1) as in the density-dependent adjustment unit 401, and determines the frequency-dependent adjustment amount F(Y1) as in the frequency-dependent adjustment unit 501. Then, in a case where the value of the R channel in a certain pixel after the comprehensive adjustment is R4, the value of the G channel in the same pixel after the comprehensive adjustment is G4, and the value of the B channel in the same pixel after the comprehensive adjustment is B4, gradation adjustment is performed using the following equations (19) to (21). The equations (19) to (21) are obtained by replacing the coefficient α in the adjustment term "α×D(Y1)" of the fourth embodiment with the adjustment amount F(Y1) of the fifth embodiment. It can be said that the equations (19) to (21) are obtained by replacing the coefficient β in the adjustment term "F(Y1)×β" of the fifth embodiment with the adjustment amount D(Y1) of the fourth embodiment. Therefore, the method of determining the sign (±) of the adjustment term "F(Y1)×D(Y1)" is the same as in the fourth embodiment and/or the fifth embodiment.

$$R4=R1\pm F(Y1)\times D(Y1) \quad (19)$$

$$G4=G1\pm F(Y1)\times D(Y1) \quad (20)$$

$$B4=B1\pm F(Y1)\times D(Y1) \quad (21)$$

As described above, in a case where the density-dependent adjustment and the frequency-dependent adjustment are combined, by adjusting the distance between two points in the L*a*b* color space to be large in the portion having a higher density or a higher frequency than a specific density or a specific frequency, which separates the relative discrimination between the mucous membrane and the blood vessel, and in the portion having a lower density or a lower frequency than the specific density or the specific frequency, it is possible to generate an image that is easy to see, and the relative discrimination between the two target tissues and the like can be adequately improved.

In the present embodiment, as described above, the color image generation unit 12 increases the distance between the color of the relatively high density and high frequency portion of the subject image and the color of the relatively low density and low frequency portion of the subject image, in the L*a*b* color space. Therefore, it is possible to improve the relative discrimination between the high density and high frequency portion and the low density and low frequency portion. In the endoscopic image, the blood vessel is the "relatively high density and high frequency portion of the subject image" and the mucous membrane is the "relatively low density and low frequency portion of the subject image". Therefore, as in the present embodiment, as described above, increasing the distance between the color of the relatively high density and high frequency portion of the subject image and the color of the relatively low density and low frequency portion of the subject image is particularly useful in endoscopic images.

Depending on the features of the subject image of the specific color image 56, the color image generation unit 12 may improve the discrimination between the relatively high density and "low" frequency portion of the subject image and relatively low density and "high" frequency portion of the subject image by the comprehensive adjustment of the present embodiment.

It is preferable that in a case where the subject image includes the blood vessel and the mucous membrane, the color image generation unit 12 increases the color difference between the blood vessel and the mucous membrane with respect to the subject image in the specific color image 56 by the gradation adjustment, the density-dependent adjustment, the frequency-dependent adjustment, or the comprehensive adjustment described in the above embodiments and modification examples. This is because the color difference between the blood vessel and the mucous membrane is directly linked to the discrimination between the blood vessel and the mucous membrane, and therefore has a particularly high importance in the diagnosis using the endoscopic image. Note that "increasing the color difference" means increasing the distance in the a*b* plane direction in the L*a*b* color space (particularly within the color gamut 80 of sRGB).

It is preferable that in a case where the subject image includes the blood vessel and the mucous membrane, the color image generation unit 12 increases the difference in brightness between the blood vessel and the mucous membrane with respect to the subject image in the specific color image 56 by the gradation adjustment, the density-dependent adjustment, the frequency-dependent adjustment, or the comprehensive adjustment described in the above embodiments and modification examples. This is because the difference in brightness between the blood vessel and the mucous membrane is directly linked to the discrimination between the blood vessel and the mucous membrane, and therefore has a particularly high importance in the diagnosis using the endoscopic image. Note that "increasing the difference in brightness" means increasing the distance in the L* axis direction in the L*a*b* color space (particularly within the color gamut 80 of sRGB). Of course, it is particularly preferable that in a case where the subject image includes a blood vessel and a mucous membrane, the color image generation unit 12 increases the color difference between the blood vessel and the mucous membrane and the difference in brightness between the blood vessel and the mucous membrane.

Figure 28:
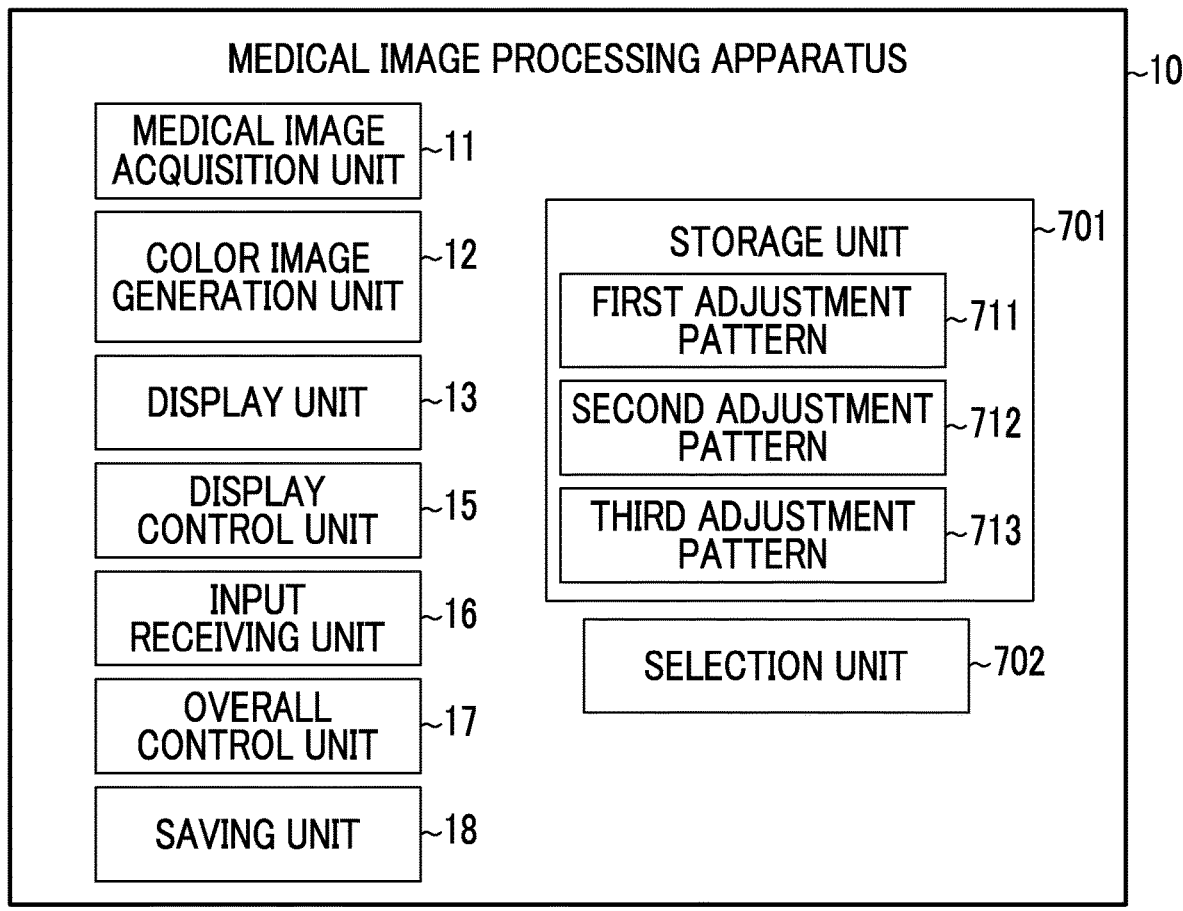
FIG. 28 is a block diagram of a medical image processing apparatus in a modification example.

In addition to the above, it is preferable that the color image generation unit 12 can easily change the mode of generating the color image 57 according to a simple operation performed by the user. In this case, as shown in FIG. 28, the medical image processing apparatus 10 comprises a storage unit 701 and a selection unit 702 in addition to the color image generation unit 12 and the like.

The storage unit 701 stores a plurality of adjustment patterns related to the balance of the color channels performed by the color image generation unit 12. The adjustment pattern is a combination of the tone curve (and/or gain) used for gradation adjustment, the parameter for determining execution or non-execution of density-dependent adjustment, the adjustment amount table 402 and coefficient α in the case of performing density-dependent adjustment, the parameter for determining execution or non-execution of frequency-dependent adjustment, the specific frequency and coefficient β for extracting a specific frequency image, the parameter for determining execution or non-execution of comprehensive adjustment, the density-dependent adjustment amount table in the case of performing comprehensive adjustment, the specific frequency for extracting the specific frequency image in the case of performing the comprehensive adjustment, and/or the parameter for determining the balance of other color channels.

In the present embodiment, the storage unit 701 has a first adjustment pattern 711, a second adjustment pattern 712, and a third adjustment pattern 713. The first adjustment pattern 711 is a group of parameters for generating the color image 57 having a tone close to that of the white light image 96, as in the first embodiment. The second adjustment pattern 712 is a group of parameters for making the mucous membrane a greenish color such as green, as in the second embodiment. The third adjustment pattern 713 is a group of parameters necessary for performing comprehensive adjustment using the density and frequency of the subject image, as in the fifth embodiment.

The selection unit 702 obtains the operation input of the user from the input receiving unit 16 to receive the selection of the adjustment pattern. Accordingly, the selection unit 702 selects any one of the plurality of adjustment patterns stored in the storage unit 701, that is, the first adjustment pattern 711, the second adjustment pattern 712, and the third adjustment pattern 713.

The color image generation unit 12 generates the color image 57 according to the adjustment pattern selected by the selection unit 702. Then, in a case where the selection unit 702 newly selects another adjustment pattern, the color image generation unit 12 switches the adjustment method of the color channels to an adjustment method according to the adjustment pattern newly selected by the selection unit 702. In this way, by making the generation method of the color image 57 a switching method using the adjustment pattern, the user can easily obtain the color image 57 in a desired mode without performing fine adjustments regarding the generation of the color image 57.

Figure 29:
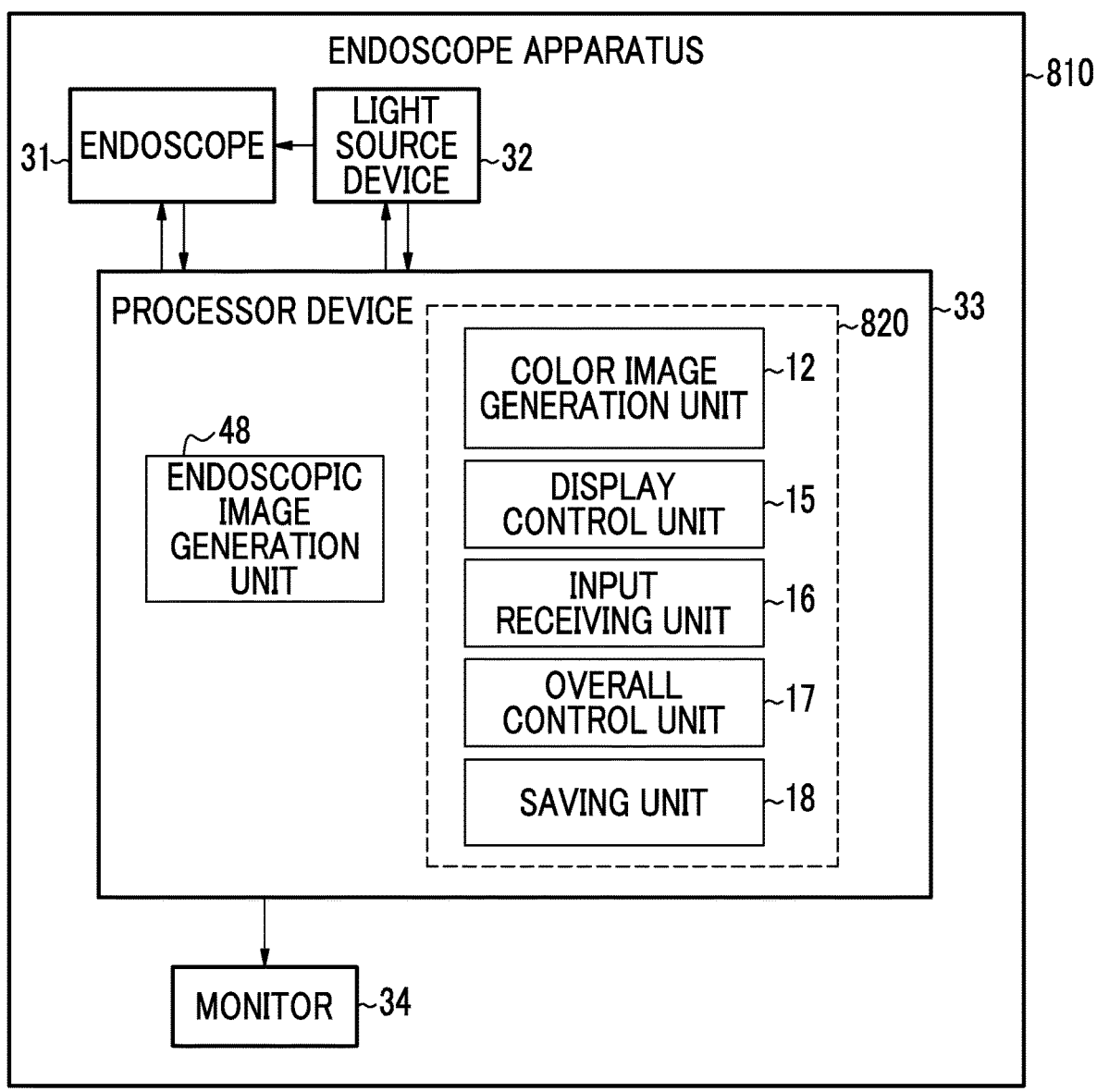
FIG. 29 is a block diagram of an endoscope apparatus including the medical image processing apparatus.

In the above embodiments and modification examples, the medical image processing apparatus 10 and the endoscope apparatus 21 are separate apparatuses. However, the endoscope apparatus 21 may include the medical image processing apparatus 10. In this case, like an endoscope apparatus 810 shown in FIG. 29, each unit 820 forming the medical image processing apparatus 10 is provided in the processor device 33. Here, the display unit 13 can share the monitor 34 of the endoscope apparatus 21. In addition, the medical image acquisition unit 11 corresponds to an "endoscopic image acquisition unit" formed by the image sensor 41 and the endoscopic image generation unit 48. Therefore, it is sufficient to provide the processor device 33 with each unit other than the medical image acquisition unit 11 and the display unit 13. The configurations of other units are similar to those of the first embodiment and the like. In addition, a new endoscope apparatus can be configured by all of the medical image processing apparatuses 10 of the above embodiments and modification examples and the endoscope apparatus 21 shown in FIG. 2.

The endoscope apparatus 810 including the medical image processing apparatus 10 is an apparatus that basically observes a subject in real time. Therefore, the endoscope apparatus 810 can execute various types of processing such as generation and display of the color image 57 in real time while capturing the endoscopic image or at any timing due to the operation of various operation units or the like.

Figure 30:
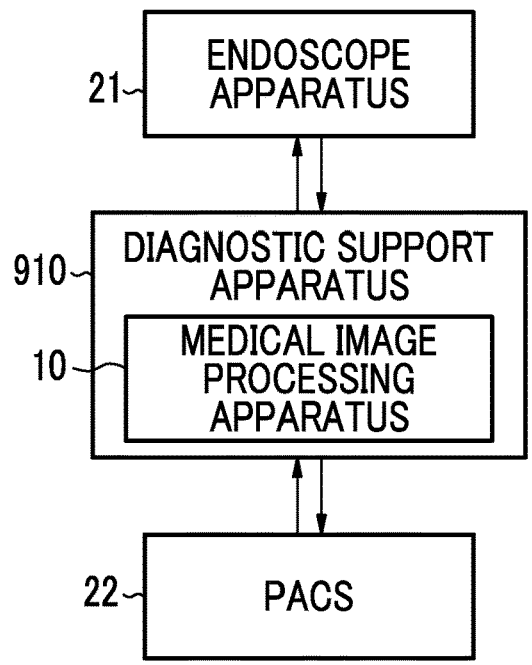
FIG. 30 is a diagnostic support apparatus including the medical image processing apparatus.
Figure 31:
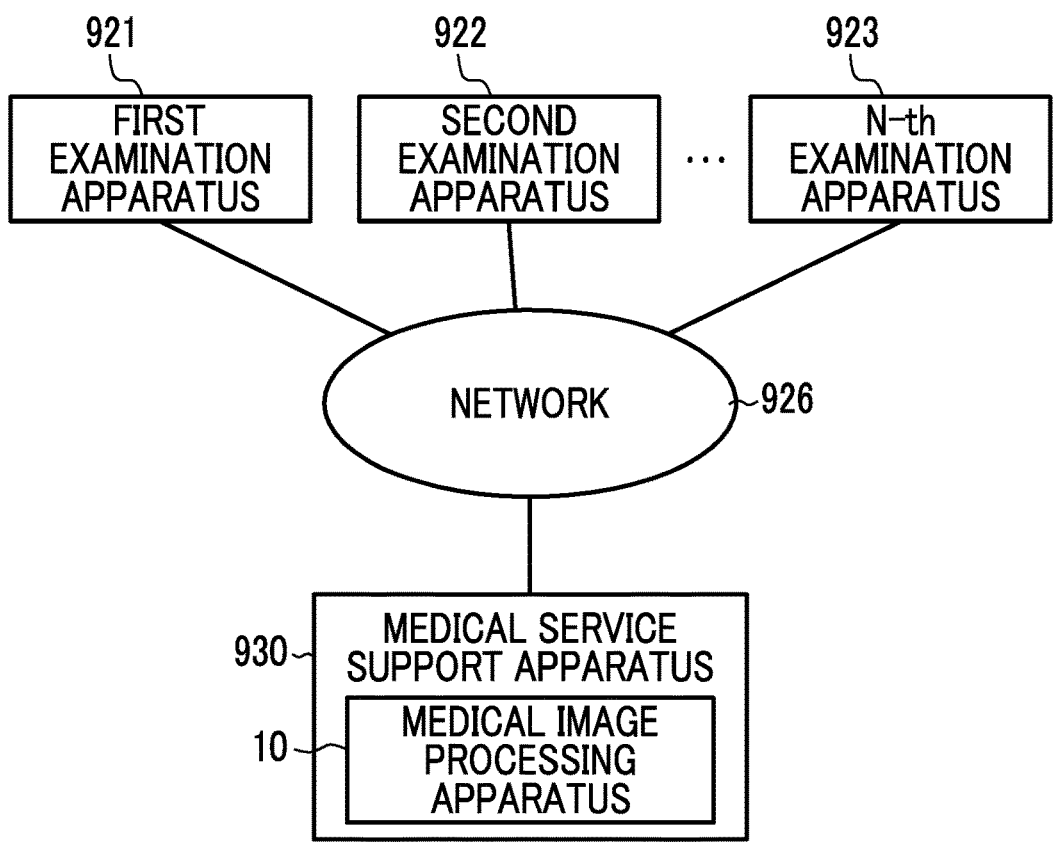
FIG. 31 is a medical service support apparatus including the medical image processing apparatus.

Although the endoscope apparatus 810 includes the medical image processing apparatus 10, as shown in FIG. 30, a diagnostic support apparatus 910 used in combination with the endoscope apparatus 21 and other modalities can include the medical image processing apparatuses 10 of the above embodiments and other modification examples. In addition, as shown in FIG. 31, for example, a medical service support apparatus 930 connected to various examination apparatuses including the endoscope apparatus 21, such as a first examination apparatus 921, a second examination apparatus 922, . . . , and an N-th examination apparatus 923, through a certain network 926 can include the medical image processing apparatuses 10 of the above embodiment and other modification examples.

In addition to this, the medical image processing apparatus 10, various apparatuses including the medical image processing apparatus 10, and various apparatuses or systems having a function of the medical image processing apparatus 10 can be used by making the following various changes or the like.

As the medical image (including the specific color image 56, and the same applies hereinafter), it is possible to use a normal light image obtained by irradiation with light in a white band or light in a plurality of wavelength bands as light in the white band.

In a case where an image obtained by irradiation with light in a specific wavelength band is used as the medical image, a band narrower than the white wavelength band can be used as a specific wavelength band.

The specific wavelength band is, for example, a blue band or a green band of a visible range.

In a case where the specific wavelength band is the blue band or the green band of a visible range, it is preferable that the specific wavelength band includes a wavelength band of 390 nm to 450 nm or a wavelength band of 530 nm to 550 nm and that light in the specific wavelength band has a peak wavelength within the wavelength band of 390 nm to 450 nm or the wavelength band of 530 nm to 550 nm.

The specific wavelength band is, for example, a red band of a visible range.

In a case where the specific wavelength band is the red band of a visible range, it is preferable that the specific wavelength band includes a wavelength band of 585 nm to 615 nm or a wavelength band of 610 nm to 730 nm and that light in the specific wavelength band has a peak wavelength within the wavelength band of 585 nm to 615 nm or the wavelength band of 610 nm to 730 nm.

The specific wavelength band can include, for example, a wavelength band in which light absorption coefficients of oxygenated hemoglobin and reduced hemoglobin are different, and light in the specific wavelength band can have a peak wavelength in the wavelength band in which light absorption coefficients of oxygenated hemoglobin and reduced hemoglobin are different.

In a case where the specific wavelength band includes a wavelength band in which the light absorption coefficients of oxygenated hemoglobin and reduced hemoglobin are different and light in the specific wavelength band has a peak wavelength in the wavelength band in which the light absorption coefficients of oxygenated hemoglobin and reduced hemoglobin are different, it is preferable that the specific wavelength band includes a wavelength band of 400±10 nm, 440±10 nm, 470±10 nm, or 600 nm to 750 nm and that light in the specific wavelength band has a peak wavelength within the wavelength band of 400±10 nm, 440±10 nm, 470±10 nm, or 600 nm to 750 nm.

In a case where the medical image is an in-vivo image of the living body, the in-vivo image can have information on fluorescence emitted from the fluorescent material in the living body.

In addition, as the fluorescence, fluorescence obtained by emitting excitation light having a peak wavelength of 390 nm to 470 nm to the inside of the living body can be used.

In a case where the medical image is an in-vivo image of the living body, the wavelength band of infrared light can be used as the specific wavelength band described above.

In a case where the medical image is an in-vivo image of the living body and the wavelength band of infrared light is used as the specific wavelength band described above, it is preferable that the specific wavelength band includes a wavelength band of 790 nm to 820 nm or 905 nm to 970 nm and that light in the specific wavelength band has a peak wavelength within the wavelength band of 790 nm to 820 nm or 905 nm to 970 nm.

The medical image acquisition unit 11 can have a special light image acquisition unit that acquires a special light image having a signal in a specific wavelength band on the basis of a normal light image obtained by emitting light in a white band or light in a plurality of wavelength bands as light in the white band. In this case, the special light image can be used as the medical image.

The signal in a specific wavelength band can be obtained by calculation based on the color information of RGB or CMY included in the normal light image.

It is possible to comprise a feature amount image generation unit that generates a feature amount image by calculation based on at least one of the normal light image obtained by emitting light in a white band or light in a plurality of wavelength bands as light in the white band or the special light image obtained by emitting light in a specific wavelength band. In this case, the feature amount image can be used as the medical image.

In the endoscope apparatus 21, a capsule endoscope can be used as the endoscope 31. In this case, the light source device 32 and a part of the processor device 33 can be mounted in the capsule endoscope.

In the above embodiments and modification examples, hardware structures of processing units for executing various kinds of processing, such as the medical image acquisition unit 11, the color image generation unit 12, the display control unit 15, the input receiving unit 16, the overall control unit 17, and the endoscopic image generation unit 48 of the endoscope apparatus 21, are various processors shown below. The various processors include a central processing unit (CPU) that is a general-purpose processor that functions as various processing units by executing software (program), a programmable logic device (PLD) that is a processor whose circuit configuration can be changed after manufacture, such as field programmable gate array (FPGA), a dedicated electrical circuit that is a processor having a dedicated circuit configuration for executing various types of processing, and the like.

One processing unit may be configured by one of various processors, or may be configured by a combination of two or more processors of the same type or different types (for example, a combination of a plurality of FPGAs or a combination of a CPU and an FPGA). In addition, a plurality of processing units may be configured by one processor. As an example of configuring a plurality of processing units by one processor, first, as represented by a computer, such as a client or a server, there is a form in which one processor is configured by a combination of one or more CPUs and software and this processor functions as a plurality of processing units. Second, as represented by a system on chip (SoC) or the like, there is a form of using a processor for realizing the function of the entire system including a plurality of processing units with one integrated circuit (IC) chip. Thus, various processing units are configured by using one or more of the above-described various processors as hardware structures.

More specifically, the hardware structure of these various processors is an electrical circuit (circuitry) in the form of a combination of circuit elements, such as semiconductor elements.

EXPLANATION OF REFERENCES

10: medical image processing apparatus
11: medical image acquisition unit
12: color image generation unit
13: display unit
15: display control unit
16: input receiving unit
17: overall control unit
18: saving unit
21, 810: endoscope apparatus
22: PACS
31: endoscope
32: light source device
33: processor device
34: monitor
41: image sensor
42: light source unit
47: light source control unit
48: endoscopic image generation unit
51: image generation unit
52: gradation adjustment unit
56: specific color image
57: color image
80: color gamut of sRGB in L*a*b* color space
86A: light gray
86B, 86C: light red
86D, 86E: light green
87A: dark gray
87B, 87C: dark red
87D: dark green
87E: dark magenta
91: thick solid line
92: broken line
96: white light image
97: thick blood vessel
98: surface blood vessel
99: middle-deep blood vessel
101: intersection
401: density-dependent adjustment unit
402: adjustment amount table
403: gray
403E: orange
501: frequency-dependent adjustment unit
601: comprehensive adjustment unit
701: storage unit
702: selection unit
711: first adjustment pattern
712: second adjustment pattern
713: third adjustment pattern
820: each unit forming medical image processing apparatus
910: diagnostic support apparatus
921: first examination apparatus
922: second examination apparatus
923: N-th examination apparatus
926: network
930: medical service support apparatus
S110 to S112: steps of operation

What is claimed is:

1. A medical image processing apparatus comprising:
a processor configured to:
acquire a specific color image obtained by imaging a subject with specific monochromatic light;
increase a difference in brightness between a blood vessel and a mucous membrane included in a subject image within the specific color image; and
generate a color image from the specific color image by assigning the brightness difference increased specific color image to a plurality of color channels and adjusting a balance of each of the color channels.

2. The medical image processing apparatus according to claim 1,
wherein the processor is configured to adjust gradation of each of the color channels by changing the balance of each of the color channels.

3. The medical image processing apparatus according to claim 2,
wherein the processor is configured to adjust a gain applied to the specific color image, the gain adjusted specific color image being assigned to the color channels before generating the color image.

4. The medical image processing apparatus according to claim 3,
wherein the processor is configured to adjust the balance of each of the color channels by changing the balance of the color channels for each pixel or for each region including a plurality of pixels.

5. The medical image processing apparatus according to claim 2,
wherein the processor is configured to adjust the balance of each of the color channels by changing the balance of the color channels for each pixel or for each region including a plurality of pixels.

6. The medical image processing apparatus according to claim 5,
wherein the processor is configured to adjust the balance of each of the color channels by adjusting the balance of the color channels depending on a density of a subject image.

7. The medical image processing apparatus according to claim 1,
wherein the processor is configured to adjust the balance of each of the color channels by changing the balance of the color channels for each pixel or for each region including a plurality of pixels.

8. The medical image processing apparatus according to claim 7,
wherein the processor is configured to adjust the balance of each of the color channels by adjusting the balance of the color channels depending on a density of a subject image.

9. The medical image processing apparatus according to claim 8,
wherein the processor is configured to increase a distance between a color of a first density portion of the subject image and a color of a second density portion of the subject image, in an L*a*b* color space, and
the first density portion has a lower density than the second density portion.

10. The medical image processing apparatus according to claim 8,
wherein the processor is configured to increase a distance between a color of a first frequency component of the subject image and a color of a second frequency component of the subject image, in an L*a*b* color space, and
the first frequency component has a lower frequency than the second frequency component.

11. The medical image processing apparatus according to claim 7,
wherein the processor is configured to adjust the balance of each of the color channels by adjusting the balance of the color channels depending on a frequency of a subject image.

12. The medical image processing apparatus according to claim 7,
wherein the processor is configured to increase a distance between a color of a second density and second frequency portion of a subject image and a color of a first density and first frequency portion of the subject image, in an L*a*b* color space,
the first density portion has a lower density than the second density portion, and
the first frequency portion has a lower frequency than the second frequency portion.

13. The medical image processing apparatus according to claim 1,
wherein where a subject image includes a mucous membrane, the processor is configured to generate the color image in which the mucous membrane is green.

14. The medical image processing apparatus according to claim 1,
wherein the monochromatic light is violet light, blue light, or green light.

15. The medical image processing apparatus according to claim 1, wherein the processor is further configured to:
store a plurality of adjustment patterns related to the balance of the color channels; and
select the adjustment pattern,
wherein the processor is configured to generate the color image according to the selected adjustment pattern, and
in a case where the processor newly selects the adjustment pattern, the processor is configured to switch an adjustment method of the color channels to an adjustment method according to the newly selected adjustment pattern.

* * * * *